(12) United States Patent
Zhang et al.

(10) Patent No.: US 9,549,986 B2
(45) Date of Patent: Jan. 24, 2017

(54) BLOCK COPOLYMER, LIQUID COMPOSITE THEREOF, NUCLEIC ACID PREPARATION, PREPARATION METHODS THEREFOR, AND USE THEREOF

(71) Applicant: Suzhou Ribo Life Science Co., Ltd., Jiangsu (CN)

(72) Inventors: Hongyan Zhang, Beijing (CN); Jun Wang, Hefei (CN)

(73) Assignee: Suzhou Ribo Life Science Co., Ltd. (CN)

( * ) Notice: Subject to any disclaimer, the term of this patent is extended or adjusted under 35 U.S.C. 154(b) by 0 days.

(21) Appl. No.: 14/354,496

(22) PCT Filed: Oct. 23, 2012

(86) PCT No.: PCT/CN2012/083377
§ 371 (c)(1),
(2) Date: Apr. 25, 2014

(87) PCT Pub. No.: WO2013/060261
PCT Pub. Date: May 2, 2013

(65) Prior Publication Data
US 2015/0093444 A1    Apr. 2, 2015

(30) Foreign Application Priority Data
Oct. 26, 2011  (CN) .......................... 2011 1 0329184

(51) Int. Cl.
| | |
|---|---|
| *A61K 47/34* | (2006.01) |
| *C08G 79/04* | (2006.01) |
| *C12N 15/113* | (2010.01) |
| *C08G 63/08* | (2006.01) |
| *A61K 9/107* | (2006.01) |
| *A61K 9/51* | (2006.01) |
| *A61K 31/7105* | (2006.01) |
| *A61K 31/713* | (2006.01) |
| *C12N 15/11* | (2006.01) |

(52) U.S. Cl.
CPC ............ *A61K 47/34* (2013.01); *A61K 9/1075* (2013.01); *A61K 9/5153* (2013.01); *A61K 31/713* (2013.01); *A61K 31/7105* (2013.01); *C08G 63/08* (2013.01); *C08G 79/04* (2013.01); *C12N 15/111* (2013.01); *C12N 15/113* (2013.01); *C12N 2310/14* (2013.01); *C12N 2320/32* (2013.01)

(58) Field of Classification Search
None
See application file for complete search history.

(56) References Cited

U.S. PATENT DOCUMENTS

2006/0147490 A1    7/2006  Bowden et al.

FOREIGN PATENT DOCUMENTS

| CN | 101474408 A | 7/2009 |
|---|---|---|
| CN | 101766817 A | 7/2010 |

OTHER PUBLICATIONS

Hein, et al. (2008) "Click Chemistry, a Powerful Tool for Pharmaceutical Sciences", Pharmaceutical Research, 25(10): 2216-30 (downloaded from NIH Public Access as 30 page document on Jun. 1, 2015).*
Sadauskas, et al. (2007) "Kupffer cells are central in the removal of nanoparticles from the Organism", Particle and Fibre Toxicology 4:10: pp. 1-7.*
International Search Report for Application No. PCT/CN2012/083377 dated Feb. 14, 2013.
Wang et al., "Biodegradable vesicular nanocarriers based on poly(3-caprolactone)-block-poly(ethyl ethylene phosphate) for drug delivery", Polymer 50 (2009), 5048-5054.

* cited by examiner

*Primary Examiner* — Robert M Kelly
(74) *Attorney, Agent, or Firm* — Lerner, David, Littenberg, Krumholz & Mentlik, LLP

(57) ABSTRACT

Provided are a polycaprolactone-polyphosphate block copolymer, a liquid composite formed by the block copolymer, a nucleic acid preparation, preparation methods for the copolymer and the liquid composite, and the use of the copolymer and the liquid composite in a nucleic acid medicine delivery system. The block copolymer prepared using the present invention has good biocompatibility, low cytotoxicity, and good biodegradability. The micelles provided in the present invention self-assemble into nano-particles in an aqueous solution, and have good stability, biocompatibility, and biodegradability, and low cytotoxicity. The preparation method is simple, has high repeatability, as a vector can protect small nucleic acids such as siRNA from biodegradation, can combine with the scale effect of nano-particles, and can be used for treating different diseases. Additionally, bonding targeting groups enable specificity recognition of different cancer cells.

24 Claims, 21 Drawing Sheets

1 Control
2 Lipo/si*HIF*, si*HIF* = 50 nM
3 MMP1.5$_{siHIF}$, si*HIF* = 50 nM
4 MMP1.5$_{siHIF}$, si*HIF* = 100 nM
5 MMP1.5$_{siHIF}$, si*HIF* = 200 nM
6 MMP1.5$_{siHIF}$, si*HIF* = 400 nM
7 MMP1.5$_{siN.C.}$, si*N.C.* = 400 nM

SEQUENCE LISTING

```
<160> NUMBER OF SEQ ID NOS: 18

<210> SEQ ID NO 1
<211> LENGTH: 21
<212> TYPE: RNA
<213> ORGANISM: Artificial Sequence
<220> FEATURE:
<223> OTHER INFORMATION: Positive-sense strand of siCDK4
<220> FEATURE:
<221> NAME/KEY: misc_feature
<222> LOCATION: (20)..(21)
```

<223> OTHER INFORMATION: n is t

<400> SEQUENCE: 1
caucguucac cgagaucugn n                                              21

<210> SEQ ID NO 2
<211> LENGTH: 21
<212> TYPE: RNA
<213> ORGANISM: Artificial Sequence
<220> FEATURE:
<223> OTHER INFORMATION: Antisense strand of siCDK4
<220> FEATURE:
<221> NAME/KEY: misc_feature
<222> LOCATION: (20)..(21)
<223> OTHER INFORMATION: n is t

<400> SEQUENCE: 2
cagaucucgg ugaacgaugn n                                              21

<210> SEQ ID NO 3
<211> LENGTH: 24
<212> TYPE: DNA
<213> ORGANISM: Artificial Sequence
<220> FEATURE:
<223> OTHER INFORMATION: Forward primer for GAPDH

<400> SEQUENCE: 3
atcaagaagg tggtgaagca ggca                                           24

<210> SEQ ID NO 4
<211> LENGTH: 21
<212> TYPE: DNA
<213> ORGANISM: Artificial Sequence
<220> FEATURE:
<223> OTHER INFORMATION: Forward primer for CDK4

<400> SEQUENCE: 4
gccttcccat cagcacagtt c                                              21

<210> SEQ ID NO 5
<211> LENGTH: 24
<212> TYPE: DNA
<213> ORGANISM: Artificial Sequence
<220> FEATURE:
<223> OTHER INFORMATION: Reverse primer for GAPDH

<400> SEQUENCE: 5
tggaagagtg ggagttgctg ttga                                           24

<210> SEQ ID NO 6
<211> LENGTH: 21
<212> TYPE: DNA
<213> ORGANISM: Artificial Sequence
<220> FEATURE:
<223> OTHER INFORMATION: Reverse primer for CDK4

<400> SEQUENCE: 6
caaagataca gccaacactc c                                              21

<210> SEQ ID NO 7
<211> LENGTH: 21
<212> TYPE: RNA
<213> ORGANISM: Artificial Sequence
<220> FEATURE:
<223> OTHER INFORMATION: Positive-sense strand of siHIF
<220> FEATURE:
<221> NAME/KEY: misc_feature

```
<222> LOCATION: (20)..(21)
<223> OTHER INFORMATION: n is t

<400> SEQUENCE: 7
cgaucaugca gcuacuacan n                                             21

<210> SEQ ID NO 8
<211> LENGTH: 21
<212> TYPE: RNA
<213> ORGANISM: Artificial Sequence
<220> FEATURE:
<223> OTHER INFORMATION: Positive-sense strand of negative control siRNA
<220> FEATURE:
<221> NAME/KEY: misc_feature
<222> LOCATION: (20)..(21)
<223> OTHER INFORMATION: n is t

<400> SEQUENCE: 8
aguucaacga ccaguagucn n                                             21

<210> SEQ ID NO 9
<211> LENGTH: 21
<212> TYPE: RNA
<213> ORGANISM: Artificial Sequence
<220> FEATURE:
<223> OTHER INFORMATION: Antisense strand of siHIF
<220> FEATURE:
<221> NAME/KEY: misc_feature
<222> LOCATION: (20)..(21)
<223> OTHER INFORMATION: n is t

<400> SEQUENCE: 9
uguaguagcu gcaugaucgn n                                             21

<210> SEQ ID NO 10
<211> LENGTH: 21
<212> TYPE: RNA
<213> ORGANISM: Artificial Sequence
<220> FEATURE:
<223> OTHER INFORMATION: Antisense strand of negative control siRNA
<220> FEATURE:
<221> NAME/KEY: misc_feature
<222> LOCATION: (20)..(21)
<223> OTHER INFORMATION: n is t

<400> SEQUENCE: 10
gacuacuggu cguugaacun n                                             21

<210> SEQ ID NO 11
<211> LENGTH: 16
<212> TYPE: DNA
<213> ORGANISM: Artificial Sequence
<220> FEATURE:
<223> OTHER INFORMATION: Forward primer for HIF-1 alpha

<400> SEQUENCE: 11
gcaagccctg aaagcg                                                   16

<210> SEQ ID NO 12
<211> LENGTH: 16
<212> TYPE: DNA
<213> ORGANISM: Artificial Sequence
<220> FEATURE:
<223> OTHER INFORMATION: Reverse primer for HIF-1 alpha

<400> SEQUENCE: 12
ggctgtccga ctttga                                                   16
```

<210> SEQ ID NO 13
<211> LENGTH: 23
<212> TYPE: RNA
<213> ORGANISM: Artificial Sequence
<220> FEATURE:
<223> OTHER INFORMATION: Positive-sense strand of siRNA for ApoB
<220> FEATURE:
<221> NAME/KEY: misc_feature
<222> LOCATION: (2)..(2)
<223> OTHER INFORMATION: n is uracil with 2' hydroxyl replaced by
      fluoro
<220> FEATURE:
<221> NAME/KEY: misc_feature
<222> LOCATION: (3)..(3)
<223> OTHER INFORMATION: n is cytosine with 2' hydroxyl replaced by
      fluoro
<220> FEATURE:
<221> NAME/KEY: misc_feature
<222> LOCATION: (5)..(5)
<223> OTHER INFORMATION: n is uracil with 2' hydroxyl replaced by fluoro
<220> FEATURE:
<221> NAME/KEY: misc_feature
<222> LOCATION: (6)..(6)
<223> OTHER INFORMATION: n is cytosine with 2' hydroxyl replaced by
      fluoro
<220> FEATURE:
<221> NAME/KEY: misc_feature
<222> LOCATION: (17)..(18)
<223> OTHER INFORMATION: n is cytosine with 2' hydroxyl replaced by
      fluoro
<220> FEATURE:
<221> NAME/KEY: misc_feature
<222> LOCATION: (21)..(21)
<223> OTHER INFORMATION: n is uracil with 2' hydroxyl replaced by fluoro
<220> FEATURE:
<221> NAME/KEY: misc_feature
<222> LOCATION: (22)..(23)
<223> OTHER INFORMATION: n is t

<400> SEQUENCE: 13
gnnannacac ugaauannaa nnn                                          23

<210> SEQ ID NO 14
<211> LENGTH: 21
<212> TYPE: RNA
<213> ORGANISM: Artificial Sequence
<220> FEATURE:
<223> OTHER INFORMATION: Positive-sense strand of negative control siRNA
<220> FEATURE:
<221> NAME/KEY: misc_feature
<222> LOCATION: (1)..(1)
<223> OTHER INFORMATION: n is uracil with 2' hydroxyl replaced by
      methoxyl
<220> FEATURE:
<221> NAME/KEY: misc_feature
<222> LOCATION: (3)..(3)
<223> OTHER INFORMATION: n is cytosine with 2' hydroxyl replaced by
      methoxyl
<220> FEATURE:
<221> NAME/KEY: misc_feature
<222> LOCATION: (5)..(5)
<223> OTHER INFORMATION: n is cytosine with 2' hydroxyl replaced by
      methoxyl
<220> FEATURE:
<221> NAME/KEY: misc_feature
<222> LOCATION: (13)..(13)
<223> OTHER INFORMATION: n is guanine with 2' hydroxyl replaced by
      methoxyl
<220> FEATURE:
<221> NAME/KEY: misc_feature
<222> LOCATION: (15)..(15)
<223> OTHER INFORMATION: n is cytosine with 2' hydroxyl replaced by
      methoxyl
<220> FEATURE:
<221> NAME/KEY: misc_feature
<222> LOCATION: (16)..(16)

```
<223> OTHER INFORMATION: n is adenine with 2' hydroxyl replaced by
      methoxyl
<220> FEATURE:
<221> NAME/KEY: misc_feature
<222> LOCATION: (20)..(21)
<223> OTHER INFORMATION: n is t

<400> SEQUENCE: 14
nununcgaac gununncgun n                                             21

<210> SEQ ID NO 15
<211> LENGTH: 25
<212> TYPE: RNA
<213> ORGANISM: Artificial Sequence
<220> FEATURE:
<223> OTHER INFORMATION: Antisense strand of siRNA for ApoB
<220> FEATURE:
<221> NAME/KEY: misc_feature
<222> LOCATION: (1)..(1)
<223> OTHER INFORMATION: n is adenine with 2' hydroxyl phosphorylated
<220> FEATURE:
<221> NAME/KEY: misc_feature
<222> LOCATION: (2)..(3)
<223> OTHER INFORMATION: n is uracil with 2' hydroxyl replaced by fluoro
<220> FEATURE:
<221> NAME/KEY: misc_feature
<222> LOCATION: (18)..(18)
<223> OTHER INFORMATION: n is uracil with 2' hydroxyl replaced by fluoro
<220> FEATURE:
<221> NAME/KEY: misc_feature
<222> LOCATION: (21)..(21)
<223> OTHER INFORMATION: n is cytosine with 2' hydroxyl replaced by
      fluoro
<220> FEATURE:
<221> NAME/KEY: misc_feature
<222> LOCATION: (24)..(25)
<223> OTHER INFORMATION: n is t

<400> SEQUENCE: 15
nnngguauuc aguguganga nacnn                                         25

<210> SEQ ID NO 16
<211> LENGTH: 21
<212> TYPE: RNA
<213> ORGANISM: Artificial Sequence
<220> FEATURE:
<223> OTHER INFORMATION: Antisense strand of negative control siRNA
<220> FEATURE:
<221> NAME/KEY: misc_feature
<222> LOCATION: (2)..(2)
<223> OTHER INFORMATION: n is cytosine with 2' hydroxyl replaced by
      methoxyl
<220> FEATURE:
<221> NAME/KEY: misc_feature
<222> LOCATION: (4)..(4)
<223> OTHER INFORMATION: n is uracil with 2' hydroxyl replaced by fluoro
<220> FEATURE:
<221> NAME/KEY: misc_feature
<222> LOCATION: (7)..(7)
<223> OTHER INFORMATION: n is cytosine with 2' hydroxyl replaced by
      fluoro
<220> FEATURE:
<221> NAME/KEY: misc_feature
<222> LOCATION: (13)..(13)
<223> OTHER INFORMATION: n is cytosine with 2' hydroxyl replaced by
      fluoro
<220> FEATURE:
<221> NAME/KEY: misc_feature
<222> LOCATION: (20)..(21)
<223> OTHER INFORMATION: n is t

<400> SEQUENCE: 16
angnganacg uunggagaan n                                             21
```

```
<210> SEQ ID NO 17
<211> LENGTH: 24
<212> TYPE: DNA
<213> ORGANISM: Artificial Sequence
<220> FEATURE:
<223> OTHER INFORMATION: Forward primer for ApoB

<400> SEQUENCE: 17
ttccagccat gggcaacttt acct                                          24

<210> SEQ ID NO 18
<211> LENGTH: 24
<212> TYPE: DNA
<213> ORGANISM: Artificial Sequence
<220> FEATURE:
<223> OTHER INFORMATION: Reverse primer for ApoB

<400> SEQUENCE: 18
tactgcaggg cgtcagtgac aaat                                          24
```

BLOCK COPOLYMER, LIQUID COMPOSITE THEREOF, NUCLEIC ACID PREPARATION, PREPARATION METHODS THEREFOR, AND USE THEREOF

CROSS-REFERENCE TO RELATED APPLICATIONS

The present application is a national phase entry under 35 U.S.C. §371 of International Application No. PCT/CN2012/083377, filed on Oct. 23, 2012, which claims priority from Chinese Patent Application No. 201110329184.2, filed Oct. 26, 2011, the disclosures of which are hereby incorporated herein by reference.

SEQUENCE LISTING

The instant application contains a Sequence Listing which has been submitted an ASCII format via EFS-Web and is hereby incorporated by reference in its entirety. Said ASCII copy, created on Apr. 21, 2014, is named Sequence Listing for Suzhou_ST25.txt and is 6,895 bytes in size.

FIELD OF THE INVENTION

The present invention relates to a block copolymer, a liquid composition containing the block copolymer, a nucleic acid preparation and the preparation methods and uses of the block copolymer, the liquid composition and the nucleic acid preparation.

BACKGROUND OF THE INVENTION

RNA interference is a technology of gene silencing mediated by double-stranded small interfering RNA (siRNA) composed of about 20 nucleotides or more. It has sequence specificity, so the small nucleic acids based on RNA interference has a great application prospect in disease treatment. However, as the molecules of small nucleic acids, including siRNA, don't have the ability to target tissues or cells, have a poor ability to penetrate cell membrane and are extremely unstable in a physiological environment, their delivery system, vector in particular, is a key issue that should be solved urgently. It is also one of the most critical factors deciding whether small nucleic acid drugs can eventually and successfully be used in clinic. At present, the small nucleic acid drugs used to treat solid tumors are under clinical trial in the world, for example: TKM-D80301 developed by Tekmira, ATU027 developed by Silence Therapeutics, and CALAA-01 developed by Calando Pharmaceutics.

Therefore, it is very important to develop delivery system and preparation of small nucleic acids with high biocompatibility, and low cytotoxicity and side effects to treat diseases.

SUMMARY OF THE INVENTION

The object of the present invention is to provide a polycaprolactone-polyphosphate block copolymer and a liquid composition formed by the block copolymer. They may be used as vectors of small nucleic acid drugs and have good stability, biocompatibility and degradability. Further, the present invention also provides a nucleic acid preparation as well as the preparation methods of the foregoing copolymer and liquid composition, and their uses in a nucleic acid drug delivery system.

According to the first aspect, the present invention provides a block copolymer consisting of Block A and Block B, wherein Block A is a polycaprolactone block, Block B is a polyphosphate block having the structural unit represented by Formula I,

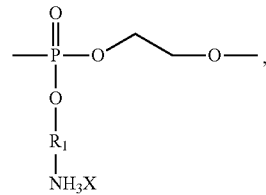

Formula I wherein, $R_1$ is an optionally substituted C2-C10 alkylene and X is a halogen;
in the block copolymer, the weight ratio between Block A and Block B is 1:0.1-5.3.

According to the second aspect, the present invention provides a method for preparing the block copolymer, which includes the following steps, (1) under conditions of ring-opening polymerization and in the presence of a ring-opening polymerization catalyst, contacting a polycaprolactone and the compound represented by Formula III with a first organic solvent, to obtain a first product,

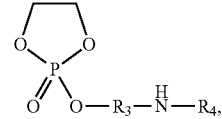

Formula III wherein, $R_3$ is an optionally substituted C2-C10 alkylene, $R_4$ is a protecting group of amino, and the weight ratio between the polycaprolactone and the compound represented by Formula III is 1:1-30;

(2) under an acidic condition, removing the protecting group of amino $R_4$ from the first product.

According to the third aspect, the present invention provides a block copolymer prepared by the foregoing method.

According to the fourth aspect, the present invention provides a liquid composition containing water and micellar nano-particles, the micellar nano-particles are formed by a second block copolymer or by a first block copolymer and a second block copolymer together, wherein the first block copolymer is a polycaprolactone-polyethylene glycol block copolymer, the second block copolymer is the foregoing block copolymer, and the molar ratio between the first block copolymer and the second block copolymer is 0-100:1.

According to the fifth aspect, the present invention provides a method for preparing the liquid composition, which includes: contacting a second block copolymer with a second organic solvent, or contacting a first block copolymer and a second block copolymer with a second organic solvent, to obtain a first solution, and contacting the first solution with water under stirring, wherein the first block copolymer is a polycaprolactone-polyethylene glycol block copolymer, the second block copolymer is the foregoing block copolymer, and the molar ratio between the first block copolymer and the second block copolymer is 0-100:1; and the second organic solvent is miscible with water.

According to the sixth aspect, the present invention provides a liquid composition prepared by the foregoing method.

According to the seventh aspect, the present invention provides a nucleic acid preparation comprising a nucleic acid as an active ingredient and a vector, wherein the vector is micellar nano-particles formed by a second block copolymer or by a first block copolymer and a second block copolymer together, the first block copolymer is polycaprolactone-polyethylene glycol block copolymer, the second block copolymer is the foregoing block copolymer, the molar ratio between the first block copolymer and the second block copolymer is 0-100:1, and the molar ratio between the second block copolymer and the nucleic acid is 0.1-1000:1.

According to the eighth aspect, the present invention provides a use of the foregoing block copolymer, liquid composition or nucleic acid preparation in the manufacture of a delivery system for a nucleic acid drug.

In the polycaprolactone-polyphosphate block copolymer of the present invention, the polycaprolactone as a hydrophobic part has the following advantages and functions: (i) relative hydrophobicity: the hydrophobic-hydrophobic interaction between polymer chains promotes self-assembly of the copolymer; (ii) biodegradability; (iii) biocompatibility; (iv) the synthesis method is simple and controllable; (v) the raw materials are cheap and thereby the cost is reduced. The polyphosphate as a hydrophilic part contains positive charges, and is the foundation for later loading nucleic acids by mainly utilizing the advantage that the polyphosphate can be easily functionalized to obtain a copolymer with side-groups containing amino functional groups.

The block copolymer and the mixed micellar nano-particles containing the block copolymer of the present invention have good biocompatibility, low cytotoxicity and biodegradability. In the present invention, the physical and chemical properties including the particle diameter and surface potential etc. of the mixed micellar particles made from the foregoing two block copolymers may be changed by adjusting the constitution of polycaprolactone-polyethylene glycol block copolymer or polycaprolactone-polyphosphate block copolymer, and the proportion of the two copolymers in the mixture system. The mixed micelles provided by the present invention are self-assembled into nano-particles with good stability in an aqueous solution. The method is simple and has high repeatability. The nano-particles, as a vector, can protect small nucleic acids such as siRNA from degradation and may be used to treat different diseases owing to their scale effect.

Further, the addition of polycaprolactone-polyethylene glycol block copolymer can further improve the stability of micelles. And by bonding different targeting groups onto the polyethylene glycol, it can also realize specificity identification of different cancer cells.

The present invention proves that the use of these micellar nano-particles carrying various therapeutic siRNAs in a plurality of cancer models may have an obvious effect in inhibiting tumor cell proliferation and migration, inhibiting vascular proliferation and realizing cancer cell cycle arrest. Further, by modification of galactosyl on micellar nano-particles, the liver is specifically targeted, and target delivery of siRNA and effective silencing of the target gene are realized in vitro and in vivo.

BRIEF DESCRIPTION OF THE DRAWINGS

The accompanying drawings provide further understanding on the present invention and constitute a part of the specification. They and the subsequent embodiments intend to explain the present invention and not to limit the present invention. In the drawings.

DETAILED DESCRIPTION OF THE INVENTION

Figure 1:
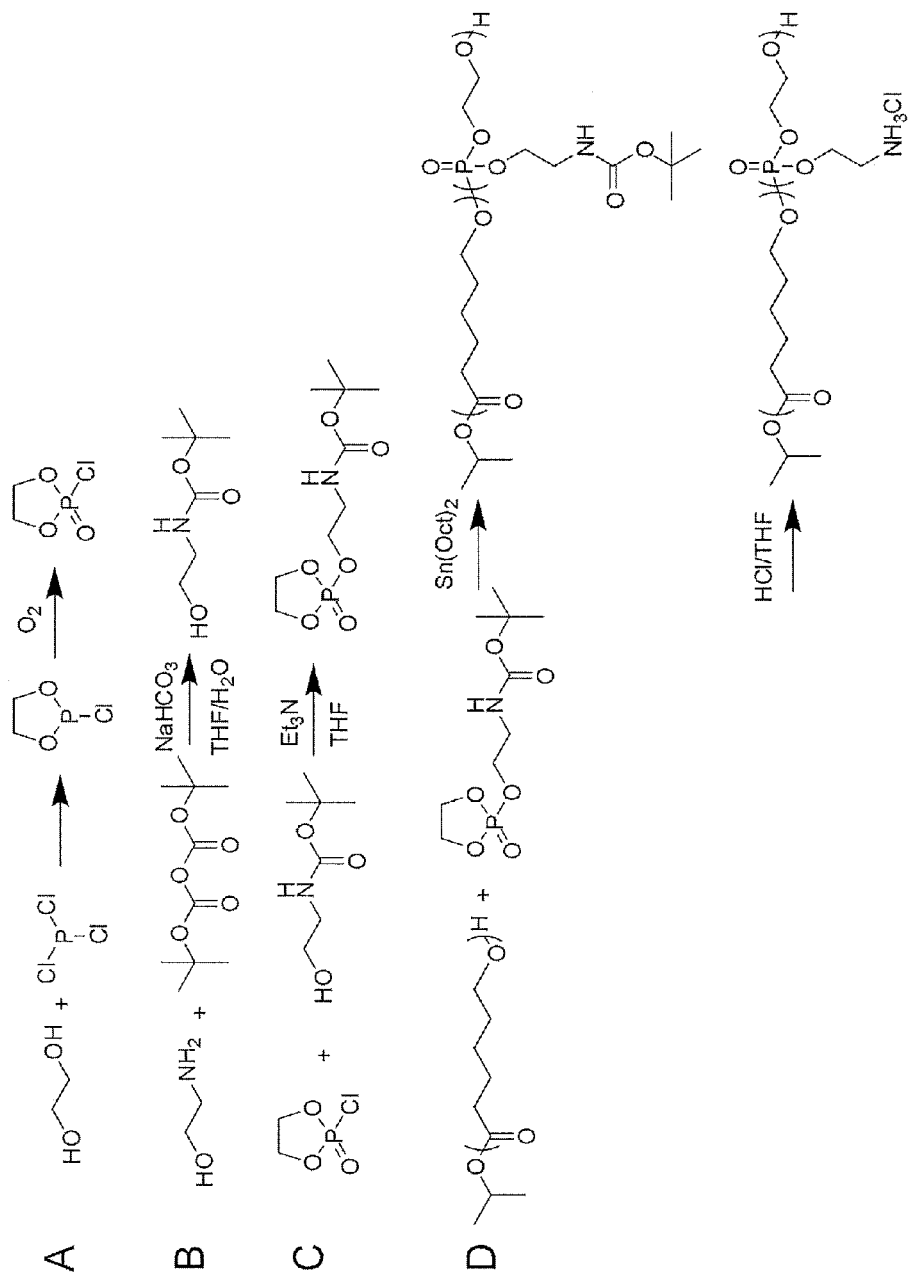
FIG. 1 shows a synthetic route of polycaprolactone-polyphosphate (PCL-PPEEA) according to an embodiment of the present invention.

The present invention provides a block copolymer consisting of Block A and Block B, wherein Block A is a polycaprolactone block, Block B is a polyphosphate block having the structural unit represented by Formula I,

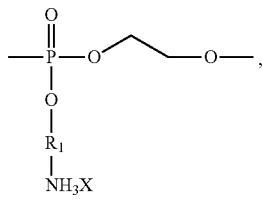

Formula I wherein, R$_1$ is C2-C10 alkylene; X is halogen, preferably Cl, Br or I, more preferably Cl; in the block copolymer, the weight ratio between Block A and Block B is 1:0.1-5.3.

In the present invention, C2-C10 alkylene is preferably optionally substituted methylene, ethylene, propylene, butylene, pentylene or hexylene, more preferably C2-C4 alkylene, most preferably ethylene.

In the present invention, the polycaprolactone (PCL) is poly ε-caprolactone.

In the block copolymer, the weight ratio between Block A and Block B is preferably 1:0.11-5.0, more preferably 1:0.12-4.0.

Preferably, the polycaprolactone block has the structure represented by Formula II and the block copolymer is an A-B diblock copolymer,

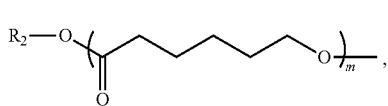

Formula II wherein, m is an integer greater than 1, preferably an integer greater than 5, R$_2$ is an optionally substituted C1-C10 alkyl.

In the present invention, the optionally substituted C1-C10 alkyl is an optionally substituted methyl, ethyl, n-propyl, isopropyl, n-butyl, iso-butyl, tert-butyl, n-pentyl, iso-pentyl, neo-pentyl or n-hexyl, preferably methyl, ethyl or isopropyl.

The average molecular weight of the polycaprolactone block is preferably 500-40000, more preferably 1000-25000. The average molecular weight of the polyphosphate block is preferably 500-10000, more preferably 1000-8000. In the present invention, the average molecular weight is determined by $^1$H NMR.

The present invention provides a method for preparing the block copolymer, which includes the following steps, (1) under the condition of ring-opening polymerization and in the presence of ring-opening polymerization catalyst, contacting polycaprolactone and the compound represented by Formula III with a first organic solvent, to obtain a first product, wherein polycaprolactone is used as a macroinitiator,

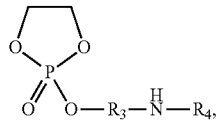

Formula III where, R$_3$ is an optionally substituted C2-C10 alkylene; R$_4$ is a protecting group of amino, preferably tert-butoxycarbonyl (Boc); and the weight ratio between the polycaprolactone and the compound represented by Formula III is 1:1-30, preferably 1:2-30.

(2) under acidic condition, removing R$_4$, the protecting group of amino, from the first product. The acidic condition is well known to those skilled in the art, for example: the condition can be realized by adding an inorganic acid, such as, hydrochloric acid, hydrobromic acid or hydroiodic acid, preferably by adding hydrochloric acid.

Preferably, the polycaprolactone has the structure represented by Formula IV,

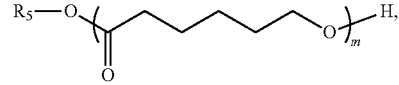

Formula IV wherein, R$_5$ is an optionally substituted C1-C10 alkyl, and m is an integer greater than 1, preferably an integer greater than 5.

According to the present invention, the average molecular weight of the polycaprolactone is preferably 500-40000, more preferably 1000-25000.

According to the present invention, the conditions of ring-opening polymerization may be conventional condition for ring-opening polymerization of cyclic phosphate in the art. Preferably, the conditions of ring-opening polymerization include temperature of 20-50° C. and duration of 1-10 hours; the ring-opening polymerization catalyst of stannous iso-caprylate (Sn(Oct)$_2$); and the first organic solvent of at least one of tetrahydrofuran (THF), dimethyl sulfoxide and toluene, preferably tetrahydrofuran.

According to the present invention, the compound represented by Formula III may be synthesized by the following synthetic method. This method includes: contacting the compound represented by Formula V with 2-chloro-2-oxo-1,3,2-dioxaphospholane under the condition of alcoholysis of acyl chloride,

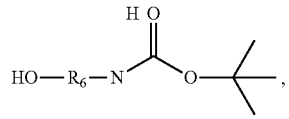

Formula V wherein, R$_6$ is an optionally substituted C2-C10 alkylene.

The condition of alcoholysis of acyl chloride is a conventional condition in the art, for example, reacting at normal temperature overnight in the presence of triethylanmine and tetrahydrofuran, under the shielding of inert gas.

The definition and the preferred range of the optionally substituted C2-C10 alkylene are the same as the above.

The compound represented by Formula V may be synthesized by the method shown in Step B in FIG. 1. The synthetic method is well known to those skilled in the related field.

The 2-chloro-2-oxo-1,3,2-dioxaphospholane is commercially available. For example, it may be purchased from Sigma-aldrich. It may also be obtained by the synthetic method shown in Step A in FIG. 1. The synthetic method is well known to those skilled in the related field.

In short, most preferably, polycaprolactone-polyphosphate diblock copolymer may be obtained through ring-opening polymerization of the cyclic phosphate monomer, with stannous iso-caprylate as the catalyst, and polycaprolactone as the macroinitiator which has hydroxyl and alkyl as terminals respectively and may have different molecular weight.

The present invention provides the block copolymer prepared by the above described method. The block copolymer is preferably PCL-PPEEA, including but not limited to: at least one of $PCL_{1000}$-$PPEEA_{5600}$, $PCL_{3300}$-$PPEEA_{1000}$, $PCL_{3300}$-$PPEEA_{5600}$, $PCL_{3300}$-$PPEEA_{8000}$ and $PCL_{25000}$-$PPEEA_{5600}$, in which the PPEEA is polyaminoethyl-ethylene phosphate, and the numerals in subscript stands are the average molecular weight of the copolymer determined by $^1$H NMR.

The present invention provides a liquid composition containing water and micellar nano-particles, in which the micellar nano-particles are formed by a second block copolymer or by a first block copolymer and a second block copolymer together, wherein the first block copolymer is a polycaprolactone-polyethylene glycol block copolymer, the second block copolymer is the foregoing block copolymer, and the molar ratio between the first block copolymer and the second block copolymer is 0-100:1, preferably 0.1-50:1, more preferably 1.1-30:1, most preferably 1.2-10:1.

According to the present invention, the particle diameter of the micellar nano-particles is preferably 10-250 nm, more preferably 20-200 nm; Zeta potential of the micellar nano-particles is preferably 10-100 mV, more preferably 30-60 mV. The particle diameter of the micellar nano-particles is the particle diameter detected by dynamic light scattering.

According to the present invention, the first block copolymer is preferably a polycaprolactone-polyethylene glycol diblock copolymer (PCL-PEG).

According to the present invention, in the first block copolymer, the average molecular weight of the polycaprolactone block is preferably 200-25000, more preferably 400-20000; and the average molecular weight of the polyethylene glycol block is 200-10000, preferably 500-5000. The PCL-PEG includes but not limited to: at least one of $PEG_{550}$-$PCL_{4600}$, $PEG_{2000}$-$PCL_{1000}$, $PEG_{2000}$-$PCL_{4600}$, $PEG_{2000}$-$PCL_{25000}$ and $PEG_{10000}$-$PCL_{4600}$.

According to the present invention, preferably, in the liquid composition, based on the volume of the liquid composition, the concentration of the first block copolymer is 0-5×10$^{-3}$ M, more preferably 1×10$^{-5}$-5×10$^{-3}$ M, most preferably 1×10$^{-4}$-1×10$^{-3}$ M; and the concentration of the second block copolymer is 1×10$^{-5}$-5×10$^{-3}$ M, most preferably 1×10$^{-4}$-1×10$^{-3}$ M (M refers to moles per liter (mol/L)).

According to the present invention, based on the volume of the liquid composition, the concentration of the micellar nano-particles is preferably 10-100 μg/ml, more preferably 20-50 μg/ml.

According to the present invention, the polyethylene glycol in the polyethylene glycol block may be modified, preferably, at least part of the polyethylene glycol block is modified by a targeting substance. The targeting substance is at least one of folic acid, saccharide, oligopeptides with cell binding function, monoclonal antibody and aptamer. Through modification by the targeting substance, the block copolymer may target the target tissues and cells. For example, acetyl galactose used in the present invention may guide the block copolymer to target the liver.

In the present invention, the polyethylene glycol block being modified by the targeting substance refers to that a covalent bond is formed therebetween. Those skilled in the art can understand that the polyethylene glycol block modified by the targeting substance is a simplified wording. For example, the polyethylene glycol block modified by acetyl galactose refers to the compound obtained after acetyl galactosyl substitutes the end group of polyethylene glycol. Moreover, the above mentioned average molecular weight of the polyethylene glycol block is calculated based on the portion of the polyethylene glycol excluding the modification portion.

The present invention does not have particular limitation to the modification position of the targeting substance. For the convenience of synthesis, preferably, the targeting substance is modified on the end group of polyethylene glycol block. The modification method is well known to those skilled in the art.

The present invention provides a method for preparing the liquid composition, which includes: contacting a second block copolymer with a second organic solvent, or contacting a first block copolymer and a second block copolymer with a second organic solvent, to obtain a first solution, and contacting the first solution with water under stirring, wherein the first block copolymer is a polycaprolactone-polyethylene glycol block copolymer, the second block copolymer is the above described block copolymer, and the molar ratio between the first block copolymer and the second block copolymer is 0-100:1, preferably 0.1-50:1, more preferably 1.1-30:1, most preferably 1.2-10:1; and the second organic solvent is miscible with water, preferably, the second organic solvent includes but not limited to at least one of dimethyl sulfoxide, acetonitrile and C1-C6 alcohol. Preferably, the C1-C6 alcohol is methanol or ethanol. The second organic solvent is preferably dimethyl sulfoxide or methanol-acetonitrile mixed solvent (mixed in equal volume).

According to the present invention, preferably, in the liquid composition, based on the volume of water, the content of the first block copolymer is 0-5×10$^{-3}$ M, preferably 1×10$^{-5}$-5×10$^{-3}$ M, most preferably 1×10$^{-4}$-1×10$^{-3}$ M; and the content of the second block copolymer is preferably 1×10$^{-5}$-5×10$^{-3}$ M, more preferably 1×10$^{-4}$-1×10$^{-3}$ M.

The first block copolymer, the average molecular weights of its blocks and the modification of the targeting substance on the polyethylene glycol block are the same as the above, and thereby do not repeat here.

According to the present invention, this method further preferably includes: dialyzing the solution obtained by contacting the first solution with water to remove the second organic solvent therein. The dialysis method is well known to those skilled in the art.

The present invention provides a liquid composition prepared by the foregoing method.

In addition to the commonly used form of liquid composition, mixed or separate solid powder of the foregoing first block copolymer and second block copolymer is also an available form, which is also included in the present invention.

The present invention provides a nucleic acid preparation comprising a nucleic acid as an active ingredient and a vector, wherein the vector is micellar nano-particles formed by a second block copolymer or by a first block copolymer and a second block copolymer together, the first block copolymer is a polycaprolactone-polyethylene glycol block copolymer, the second block copolymer is the above described block copolymer, and the molar ratio between the first block copolymer and the second block copolymer is 0-100:1, preferably 0.1-50:1, more preferably 1.1-30:1, most preferably 1.2-10:1; and the molar ratio between the second block copolymer and the nucleic acid is 0.1-1000:1, preferably 5-250:1.

According to the present invention, preferably, the molar ratio between nitrogen atoms in the vector and phosphorus atoms in the main chain of the nucleic acid is 1-100:1, more preferably 1-30:1, most preferably 2-10:1.

The particle size and Zeta potential of the micellar nano-particles are the same as above, and thus the description thereof is omitted here.

The first block copolymer, the average molecular weights of its blocks and the modification of the targeting substance on the polyethylene glycol block are the same as above, and thus the description thereof is omitted here.

According to the present invention, the nucleic acids as active ingredient may be single-stranded or double-stranded DNA, single-stranded or double-stranded RNA, oligonucleotides or polynucleotides, preferably, non-coding RNA, more preferably, at least one of siRNA, microRNA, shRNA, antisense RNA and aptamer.

According to the present invention, the nucleic acid preparation may further contain an auxiliary ingredient which may enhance the stability of siRNA, maintain and enhance the inhibitory effect of siRNA and promote targeting of siRNA. The examples of the auxiliary ingredient may be at least one of phospholipid, polypeptide, protein, polysaccharide and other polymers and macromolecular materials. For example, in order to promote siRNA to enter cells, lipophilic cholesterol, lipoprotein, vitamin E or the like may be introduced to 3'-terminal of one strand of siRNA. Lipophilic groups may bond to siRNA by a covalent bond, thus facilitate the siRNA to pass through the cell membrane comprising lipid bilayer to interact with target mRNA in the cell. Stability and bioactivity of the siRNA may also be enhanced by non-covalent bond, for example: bonding phospholipid molecules, polypeptides or polysaccharide by hydrophobic bond or ionic bond. There isn't particular limitation to the amount of the auxiliary ingredient in the composition, as long as it can maintain and/or enhance the import efficiency, stability and inhibitory effect of siRNA.

In the present invention, the nucleic acid preparation is preferably a liquid preparation. The liquid preparation may be prepared by adopting phosphate buffer solution with pH 4.0-9.0, tris(hydroxymethyl) aminomethane hydrochloride buffer solution with pH 7.5-8.5 or normal saline or phosphate buffer solution with pH 5.5-8.5. Preferably, phosphate buffer solution with pH 4.0-9.0 is used to prepare the liquid preparation provided in the present invention. The liquid preparation may further contain a protective agent and/or an osmotic pressure regulator. The protective agent is one or more selected from inositol, sorbitol and sucrose. The osmotic pressure regulator may be sodium chloride and/or potassium chloride. Taking a liquid preparation for injection for an example, the content of the protective agent may be 0.01-30 wt %. There isn't particular limitation to the content of the osmotic pressure regulator as long as it can maintain the osmotic pressure of the liquid preparation at 200-700 milliosmol/kg. When the nucleic acid preparation in a liquid form is administrated to animal or human individuals, its dosage may be conventional dosage in the art. For example, the dosage of single injection may be in a range of 1-10 g/kg of body weight. During actual use, the dosage may be determined based on various parameters, particularly based on the age, body weight and symptoms of the animal or human individuals.

When the nucleic acid preparation is a liquid preparation, based on the volume of the nucleic acid preparation, the concentration of the micellar nano-particles is preferably 10-100 μg/ml, more preferably 20-50 μg/ml.

The present invention also provides use of the foregoing block copolymer, liquid composition or nucleic acid preparation in the manufacture of a delivery system for a nucleic acid drug.

The nucleic acid drug may be a nucleic acid drug that is capable of treating cancers, preferably treating lung cancer, prostate cancer or liver cancer.

The present invention will now be further described in details by referring to the following examples.

In the examples of the present invention, ε-caprolactone (CL, Acros), purity ≥99%, was refluxed for 24 h with $CaH_2$ in the atmosphere of $N_2$, and evaporated out under a reduced pressure before use. Aluminum isopropoxide (made by Sinopharm Chemical Reagent Co., Ltd.) was distilled three times under a reduced pressure, quenched by liquid nitrogen after held at 150° C. for 2 h, dissolved in anhydrous toluene for future use. Stannous iso-caprylate (made by Sinopharm Chemical Reagent Co., Ltd.) was co-boiled with p-xylene twice and then distilled under a reduced pressure, and the collected fraction at 152° C. (20-40 Pa) was used in later polymerization reaction. Phosphorus trichloride and ethylene glycol were re-evaporated before use. Dichloromethane was refluxed with phosphorus pentoxide for 24 h, and evaporated out before use. Triethylamine was refluxed successively with phthalic anhydride, NaOH and $CaH_2$ each for 24 h, and evaporated out before use. Tetrahydrofuran (THF) was refluxed with Na—K alloy, and evaporated out before use. Diethyl ether and toluene were respectively refluxed and dried with sodium sand and evaporated out before use. The adopted polyethylene glycol monomethyl ether-polycaprolactone was bought from Changsha PassKey Instrument Co., Ltd. Other chemical reagents were all analytically pure reagents. Conventional molecular biological steps were conducted in reference to Molecular Cloning (Cold Spring Harbor Laboratory Press, Edition 3) or according to product specifications of the commercial reagents.

EXAMPLE 1

This example is intended to illustrate the synthesis and characterization of polycaprolactone-polyphosphate (PCL-PPEEA).

(I) Synthesis and characterization of 2-(N-tert-butoxycarbonyl-amino)ethoxy-2-oxo-1,3,2-dioxaphospholane (PEE-ABoc) cyclic phosphate monomer (1) Synthesis of 2-chloro-2-oxo-1,3,2-dioxaphospholane (COP)

The synthetic route of COP is shown in Step A of FIG. 1. The particular steps were: dropwise adding 301 ml of dichloromethane solution containing 3.25 mol/L ethylene glycol into 300 ml of dichloromethane solution containing 3.26 mol/L phosphorus trichloride; continuing to react for 0.5 h at room temperature after addition; removing the solvent by evaporation under a reduced pressure, evaporating twice under a reduced pressure to obtain the product, then dissolving the product in benzene and taking oxidation reaction by inputting $O_2$ for three days until the reaction was completed, distilling under the reduced pressure (20 Pa) and collecting the fraction at 72° C. to obtain COP.

(2) Synthesis and characterization of N-tert-butoxycarbonyl-amino ethyl alcohol (EABoc)

The synthetic route is shown in Step B of FIG. 1. The particular steps were: adding 6.1 g (0.10 mol) of ethanolamine, 100 ml of THF and 100 ml of ultrapure water in turn in a 250 ml 3-neck flask under stirring until thoroughly dissolved, then adding 8.4 g (0.1 mol) of sodium bicarbonate and 21.8 g (0.1 mol) of di-tert-butyl dicarbonate continuously; reacting at 0° C. for 30 min, then naturally raising the temperature to room temperature and reacting overnight; extracting the reaction liquid with 100 ml of diethyl ether twice and drying the organic phase with anhydrous sodium sulfate; removing the solvent under a reduced pressure, to obtain the product, with a yield of 95%.

Figure 2A:
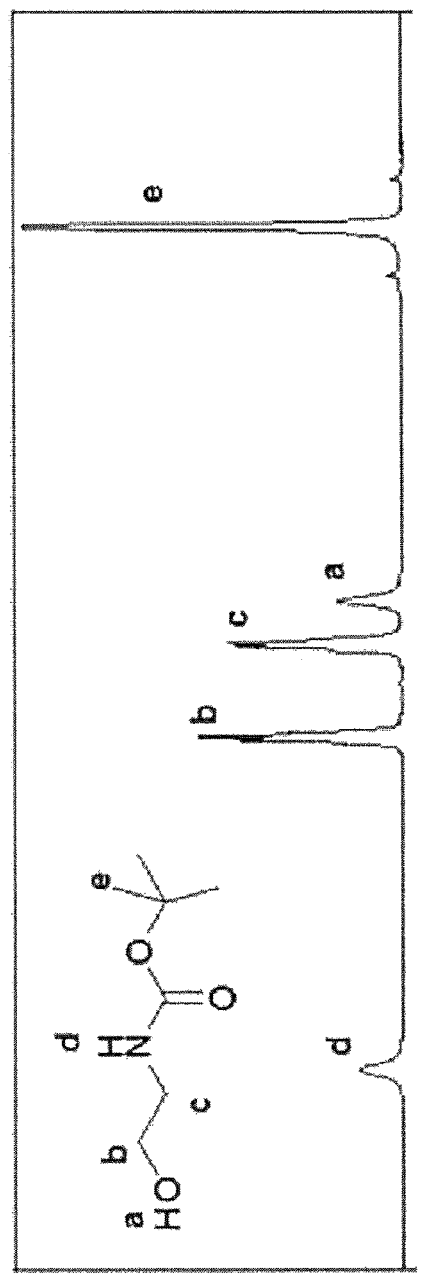
FIG. 2A is $^1$H NMR spectrum of N-tert-butoxycarbonyl-amino ethanol.

The product was analyzed by $^1$H NMR. The $^1$H NMR spectrum is shown in FIG. 2A. FIG. 2A indicates that all proton assignments and integrals agree with the structure, so it is confirmed that the product is EABoc.

(3) Synthesis and characterization of 2-(N-tert-butoxycarbonyl-amino)ethoxy-2-oxo-1,3,2-dioxaphospholane (PEEABoc)

The synthetic route is shown in Step C of FIG. 1. The particular steps were: dropwise adding THF (30 ml) solution containing COP (14.25 g, 0.1 mol) into THF (120 ml) solution containing EABoc (16.10 g, 0.1 mol) and triethylamine (10.12 g, 0.1 mol) in a low temperature reaction bath at −5° C. and reacting overnight; filtering the reaction solution under the shielding of $N_2$ to obtain the filtrate, concentrating the filtrate, precipitating it with 400 ml of dried cold diethyl ether, removing the supernate and sucking the precipitate by an oil pump to dry it.

The dried precipitate was analyzed by $^1$H NMR and $^{13}$C-NMR. The $^1$H NMR spectrum is shown in FIG. 2B, and the $^{13}$C-NMR spectrum is shown in FIG. 2C.

Figure 2B:
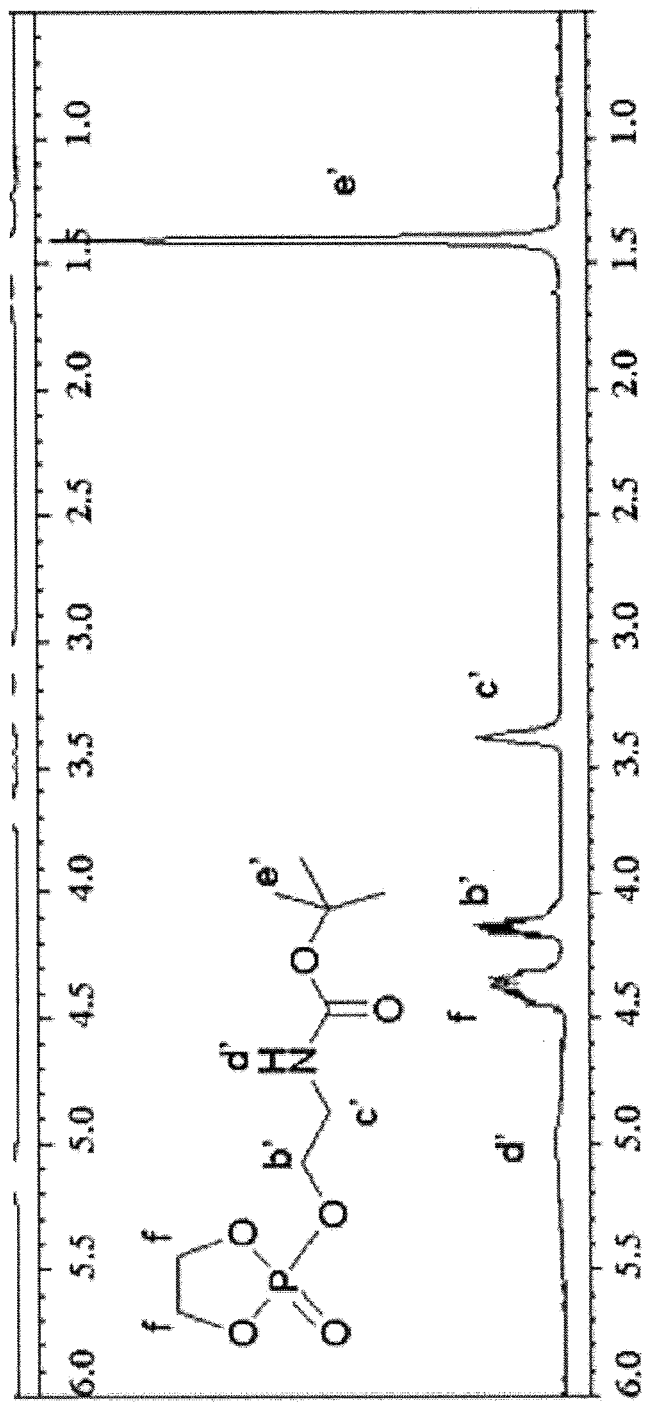
FIG. 2B is $^1$H NMR spectrum of 2-(N-tert-butoxycarbonyl-amino)ethoxy-2-oxo-1,3,2-dioxaphospholane.
Figure 2C:
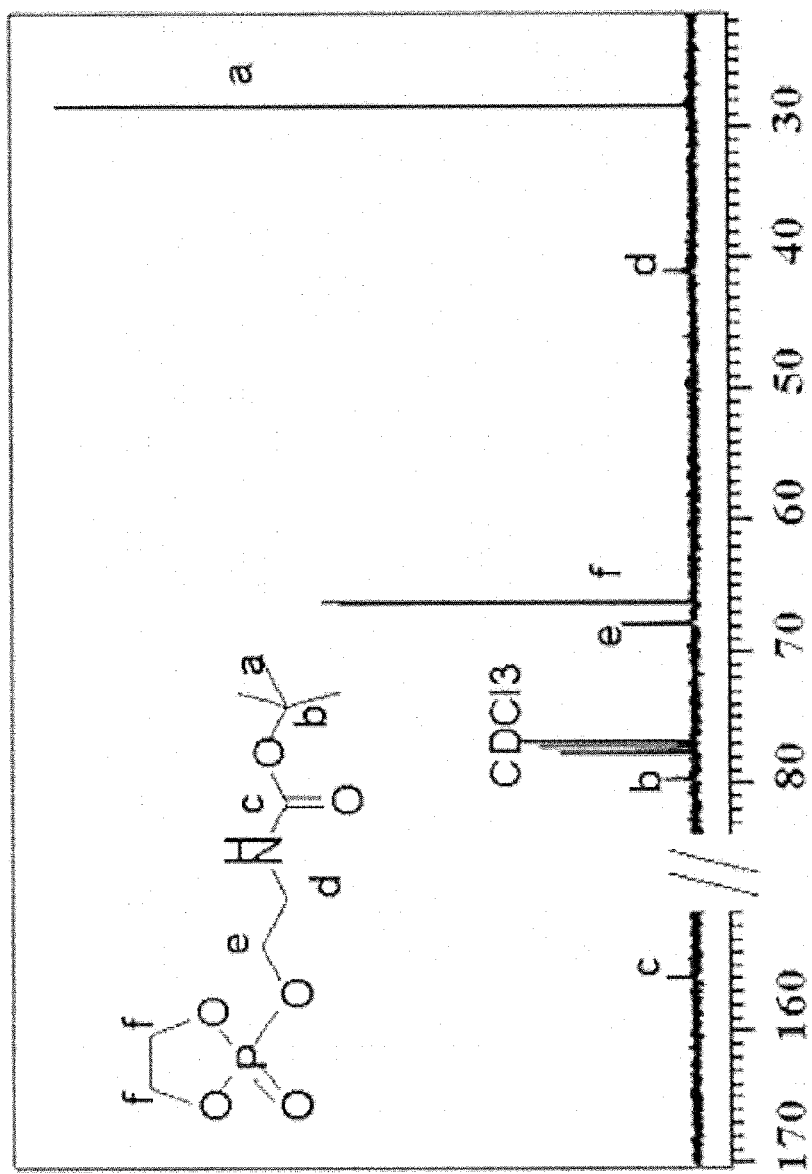
FIG. 2C is $^{13}$C-NMR spectrum of 2-(N-tert-butoxycarbonyl-amino)ethoxy-2-oxo-1,3,2-dioxaphospholane.

FIG. 2B indicates 1.43 ppm singlet belongs to the nine protons of tert-butyl, 3.36 ppm and 4.12 ppm triplets respectively belong to the two protons on segments —OCH$_2$CH$_2$NH— and —OCH$_2$CH$_2$NH—, and 4.36 ppm multiplet belongs to the four protons on phosphate ring —OCH$_2$CH$_2$O—. In FIG. 2C, the chemical shift of each carbon is stated. The above NMR spectra prove the dried precipitate is PEEABoc.

(II) Synthesis and Characterization of Polycaprolactone-Polyphosphate Diblock Copolymer (PCL-PPEEA)

(1) Synthesis and Characterization of PCL Macroinitiator

The hydroxyl-terminated polycaprolactone macroinitiator with different molecular weight was prepared by polymerization of caprolactone monomers, which was initiated at room temperature in the presence of aluminum isopropoxide as the initiator and catalyst in toluene. By adjusting the charge ratio between caprolactone and aluminum isopropoxide, polycaprolactone polymer with different molecular weight may be obtained.

Aluminum isopropoxide was used as the initiator to prepare the polymer. The polymerization reaction was operated in a glove box. The particular experimental steps of the synthesis were as follows:

1) After around-bottom flask to be used in the reaction was subjected to vacuumizing, flame drying and nitrogen filling several times, it was put into the glove box;

2) The materials were charged according to the proportion shown in Table 1: adding caprolactone (CL) monomer and toluene to the flask, and adding aluminum isopropoxide under stirring at room temperature to start the polymerization;

3) The resultant product was moved out of the glove box after several hours' reaction, acetic acid in an amount of 10 times the weight of aluminum isopropoxide was added to terminate the reaction, the reaction solution was then concentrated to remove toluene and dropewise added into cold diethyl ether, the precipitate was collected and sucked and dried by an oil pump to constant weight, to obtain the product.

By adjusting the charge ratio (molar ratio), PCL product with different molecular weight may be obtained. Its average molecular weight may be determined through $^1$H NMR analysis, as shown in Table 1.

TABLE 1

| CL monomer:aluminum isopropoxide (molar ratio) | PCL [a] |
|---|---|
| 9:1 | PCL$_{1000}$ |
| 30:1 | PCL$_{3300}$ |
| 220:1 | PCL$_{25000}$ |

[a] The subscript numerals indicates the molecular weight of the polymer obtained by $^1$H NMR The number-average molecular weight (Mn) and the molecular weight distribution (PDI, molecular weight distribution width index) of PCL, which were analyzed by gel permeation chromatography (GPC) using polystyrene as a standard, are shown in Table 2.

TABLE 2

| PCL | Mn(g/mol) [a] | Mn(g/mol) [b] | PDI [a] |
|---|---|---|---|
| PCL$_{1000}$ | 2200 | 1000 | 1.09 |
| PCL$_{3300}$ | 6100 | 3300 | 1.06 |
| PCL$_{25000}$ | 54300 | 24800 | 1.05 |

[a] determined by GPC;
[b] determined by $^1$H NMR.

(2) Synthesis and Characterization of Polycaprolactone-Polyphosphate Diblock Copolymer The polymer was prepared in a glove box by using PCL as the initiator and stannous iso-caprylate as catalyst. Before the reaction, PCL macroinitiator was treated by azeotropic distillation with dried toluene twice and then sucked till dry under a reduced pressure. The synthetic route is shown in Step D of FIG. 1. The particular steps were as follows:

1) After around-bottom flask to be used in the reaction was subjected to vacuumizing, flame drying and nitrogen filling several times, it was put into the glove box;

2) The materials were charged according to the proportion shown in Table 1: adding PCL, PEEABoc and THF to the flask and ensuring the initial concentration of PEEABoc was 2 mol/L; and adding Sn(Oct)$_2$ after stirred at 30° C. for 30 min;

3) The reaction liquid was concentrated after 3 h's reaction, and was added in 10:1 (v/v) diethyl ether/methanol mixed solvent at 0° C. to precipitate the product, the mixture was filtered and the solid was sucked till dry to obtain PCL-PPEEABoc;

4) In 10 ml of anhydrous THF, 1 g of the above polymer was dissolved, and 20 ml of 6 MHCl/THF solution was added therein so that the final concentration of HCl was 4 M, the solution was stirred and reacted at 0° C. for 2 h, then was concentrated, and the resultant was precipitates with cold diethyl ether, then filtered, and the solid was sucked till dry to obtain PCL-PPEEA polymer. With different charge ratios (molar ratios), different PCL-PPEEABoc polymer were synthesized as shown in Table 3.

TABLE 3

| PCL | PPEEABoc:PCL:Sn(Oct)$_2$ (molar ratio) | PCL-PPEEABoc $^a$ |
|---|---|---|
| PCL$_{1000}$ | 60:1:1 | PCL$_{1000}$-PPEEABoc$_{5300}$ |
| PCL$_{3300}$ | 20:1:1 | PCL$_{3300}$-PPEEABoc$_{1600}$ |
| PCL$_{3300}$ | 60:1:1 | PCL$_{3300}$-PPEEABoc$_{5600}$ |
| PCL$_{3300}$ | 90:1:1 | PCL$_{3300}$-PPEEABoc$_{8000}$ |
| PCL$_{25000}$ | 60:1:1 | PCL$_{25000}$-PPEEABoc$_{4800}$ |

The Mn and PDI of the PCL-PPEEABoc copolymers were analyzed by GPC using polystyrene as standard. It should be noted that after deprotection, PCL-PPEEA can hardly be characterized by GPC, thus the Mn and PDI listed are for PCL-PPEEABoc before deprotection. PCL-PPEE-ABocs and PCL-PPEEAs were analyzed by $^1$H NMR to determine their average molecular weights. The degree of polymerization, Mn and PDI of the PCL-PPEEABocs are shown in Table 4.

TABLE 4

| PCL-PPEEABoc | Mn$^a$ (g/mol) | Mn$^b$ (g/mol) | PDI$^a$ | PCL-PPEEA | Mn$^b$ (g/mol) |
|---|---|---|---|---|---|
| PCL$_{1000}$-PPEEABoc$_{5300}$ | 9700 | 6300 | 1.20 | PCL$_{1000}$-PPEEA$_{3300}$ | 4300 |
| PCL$_{3300}$-PPEEABoc$_{1600}$ | 6400 | 4900 | 1.29 | PCL$_{3300}$-PPEEA$_{1000}$ | 4300 |
| PCL$_{3300}$-PPEEABoc$_{5600}$ | 11200 | 8900 | 1.26 | PCL$_{3300}$-PPEEA$_{3500}$ | 6800 |
| PCL$_{3300}$-PPEEABoc$_{8000}$ | 16200 | 11300 | 1.35 | PCL$_{3300}$-PPEEA$_{5000}$ | 8300 |
| PCL$_{25000}$-PPEEABoc$_{4800}$ | 61500 | 29600 | 1.40 | PCL$_{25000}$-PPEEA$_{3000}$ | 27800 |

$^a$determined by GPC;
$^b$determined by $^1$H NMR.

EXAMPLE 2

This example is intended to illustrate the preparation and characterization of the mixed micelles of PCL-PPEEA and PCL-PEG.

(1) Preparation of the Mixed Micellar Nano-Particles

The mixed micellar nano-particles were prepared by the dialysis method: mixing the two block polymers PCL-PPEEA and PCL-PEG with different molar ratios (shown in Table 5), dissolving them in the organic solvent of acetonitrile:methanol=1:1, dropwise adding the solution into ultra-pure water (1 mg/ml) under stirring, and dialyzing in a dialysis bag (molecular weight cutoff was 2 k) to remove the organic solvent after stirring for a half hour.

(2) Measurement of Particle Size and Zeta Potential of the Mixed Micelles

Malvern ZetasizerNanao ZS90 dynamic light scattering spectrometer was used to detect the particle size and potential distribution of the different mixed micellar nano-particles with the concentration of the nano-particles of 0.1 mg/ml.

Table 5 shows the particle size and potential obtained by mixing different polymers with different molar ratios (PCL-PPEEA:PCL-PEG). From Table 5, the particle size of the obtained mixed micellar nano-particles was mainly in the range of 20-200 nm and the Zeta potential was mainly in the range of 30-60 mV, while under the same condition of measurement, the nano-particles formed only from PCL$_{4400}$-PEG$_{2000}$ had particle size of 260 nm and Zeta potential of 2.3.

Figure 3:
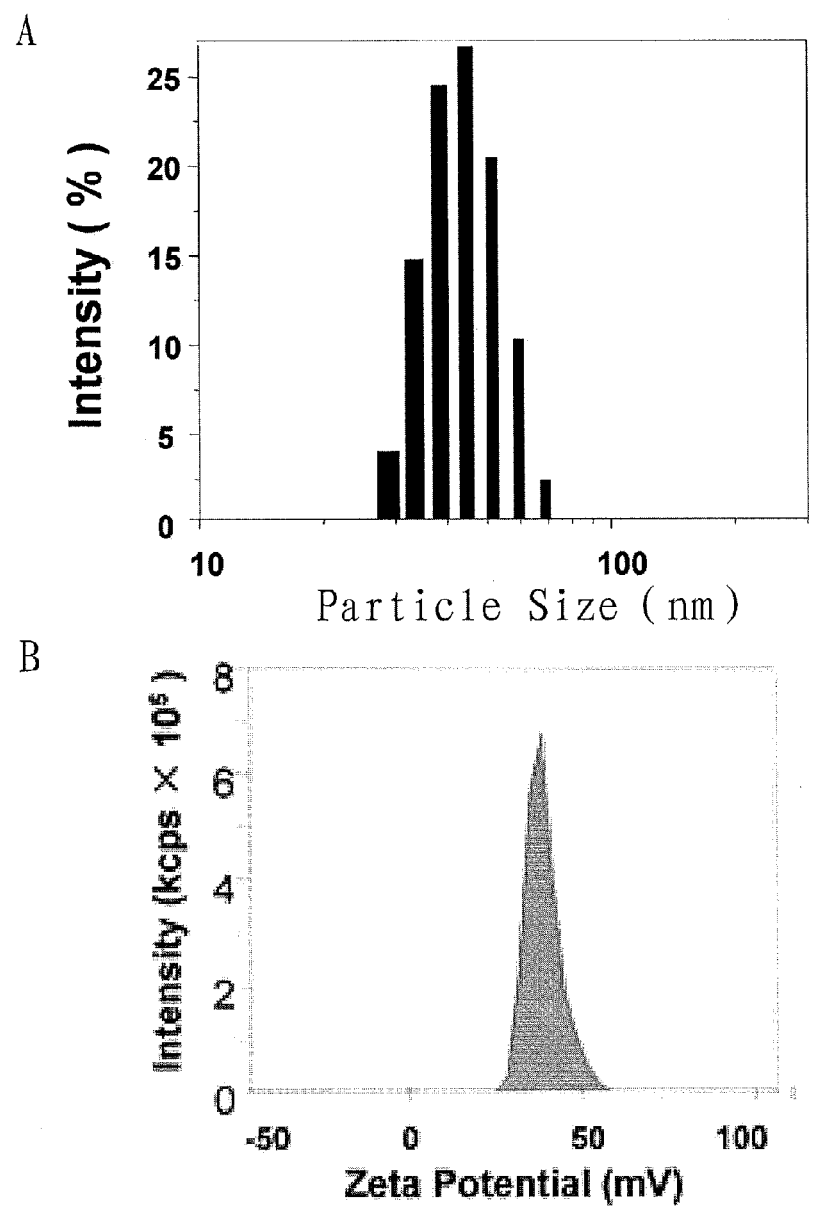
FIG. 3 is the particle size distribution diagram (A) and potential distribution diagram (B) of the mixed micelles prepared from $PCL_{3300}$-$PPEEA_{3500}$ and $PCL_{4400}$-$PEG_{2000}$ at the molar ratio of 1:1.5 (MMP1.5).

The particle size and potential distribution of the mixed micelles obtained from PCL$_{3300}$-PPEEA$_{3500}$ and PCL$_{4400}$-PEG$_{2000}$ at molar ratio of 1:1.5 are shown in FIG. 3, which shows the particle size and potential distribution of the mixed micellar nano-particles have good uniformity.

TABLE 5

| PCL-PPEEA | PCL-PEG | Molar ratio | Particle size (nm) | Potential (mV) |
|---|---|---|---|---|
| PCL$_{3300}$-PPEEA$_{3500}$ | PCL$_{4400}$-PEG$_{2000}$ | 1:0 | 80 | 56 |
| PCL$_{3300}$-PPEEA$_{3500}$ | PCL$_{4400}$-PEG$_{2000}$ | 1:0.3 | 85 | 60 |
| PCL$_{3300}$-PPEEA$_{3500}$ | PCL$_{4400}$-PEG$_{2000}$ | 1:0.6 | 83 | 57 |
| PCL$_{3300}$-PPEEA$_{3500}$ | PCL$_{4400}$-PEG$_{2000}$ | 1:1 | 81 | 55 |
| PCL$_{3300}$-PPEEA$_{3500}$ | PCL$_{4400}$-PEG$_{2000}$ | 1:1.5 | 40 | 54 |
| PCL$_{3300}$-PPEEA$_{3500}$ | PCL$_{2500}$-PEG$_{500}$ | 1:1.5 | 156 | 58 |
| PCL$_{3300}$-PPEEA$_{3500}$ | PCL$_{400}$-PEG$_{2000}$ | 1:1.5 | 105 | 50 |
| PCL$_{3300}$-PPEEA$_{3500}$ | PCL$_{13500}$-PEG$_{2000}$ | 1:1.5 | 198 | 36 |
| PCL$_{3300}$-PPEEA$_{3500}$ | PCL$_{4000}$-PEG$_{5000}$ | 1:1.5 | 145 | 32 |
| PCL$_{1000}$-PPEEA$_{3300}$ | PCL$_{4400}$-PEG$_{2000}$ | 1:1.5 | 65 | 58 |
| PCL$_{1000}$-PPEEA$_{3300}$ | PCL$_{2500}$-PEG$_{500}$ | 1:1.5 | 48 | 55 |
| PCL$_{1000}$-PPEEA$_{3300}$ | PCL$_{400}$-PEG$_{2000}$ | 1:1.5 | 29 | 42 |
| PCL$_{1000}$-PPEEA$_{3300}$ | PCL$_{13500}$-PEG$_{2000}$ | 1:1.5 | 83 | 33 |
| PCL$_{1000}$-PPEEA$_{3300}$ | PCL$_{4000}$-PEG$_{5000}$ | 1:1.5 | 56 | 47 |
| PCL$_{3300}$-PPEEA$_{1000}$ | PCL$_{4400}$-PEG$_{2000}$ | 1:1.5 | 92 | 45 |
| PCL$_{3300}$-PPEEA$_{1000}$ | PCL$_{2500}$-PEG$_{500}$ | 1:1.5 | 130 | 54 |
| PCL$_{3300}$-PPEEA$_{1000}$ | PCL$_{400}$-PEG$_{2000}$ | 1:1.5 | 112 | 39 |
| PCL$_{3300}$-PPEEA$_{1000}$ | PCL$_{13500}$-PEG$_{2000}$ | 1:1.5 | 187 | 31 |
| PCL$_{3300}$-PPEEA$_{1000}$ | PCL$_{4000}$-PEG$_{5000}$ | 1:1.5 | 103 | 42 |
| PCL$_{3300}$-PPEEA$_{5000}$ | PCL$_{4400}$-PEG$_{2000}$ | 1:1.5 | 96 | 50 |
| PCL$_{3300}$-PPEEA$_{5000}$ | PCL$_{2500}$-PEG$_{500}$ | 1:1.5 | 128 | 59 |
| PCL$_{3300}$-PPEEA$_{5000}$ | PCL$_{400}$-PEG$_{2000}$ | 1:1.5 | 110 | 52 |
| PCL$_{3300}$-PPEEA$_{5000}$ | PCL$_{13500}$-PEG$_{2000}$ | 1:1.5 | 192 | 37 |
| PCL$_{3300}$-PPEEA$_{5000}$ | PCL$_{4000}$-PEG$_{5000}$ | 1:1.5 | 164 | 45 |
| PCL$_{25000}$-PPEEA$_{3000}$ | PCL$_{4400}$-PEG$_{2000}$ | 1:1.5 | 113 | 43 |
| PCL$_{25000}$-PPEEA$_{3000}$ | PCL$_{2500}$-PEG$_{500}$ | 1:1.5 | 132 | 57 |
| PCL$_{25000}$-PPEEA$_{3000}$ | PCL$_{400}$-PEG$_{2000}$ | 1:1.5 | 108 | 52 |
| PCL$_{25000}$-PPEEA$_{3000}$ | PCL$_{13500}$-PEG$_{2000}$ | 1:1.5 | 185 | 31 |
| PCL$_{25000}$-PPEEA$_{3000}$ | PCL$_{4000}$-PEG$_{5000}$ | 1:1.5 | 96 | 38 |

(3) Detection of Stability of the Mixed Micellar Nano-Particles in Serum

PCL$_{3300}$-PPEEA$_{3500}$ and PCL$_{4400}$-PEG$_{2000}$ were used to prepare mixed micelles with different molar ratios. Supposing the molar ratio of PCL$_{4400}$-PEG$_{2000}$/PCL$_{3300}$-PPEEA$_{3500}$ was x, then the mixed micellar nano-particles were named as MMPx, and the micelles prepared only from PCL$_{3300}$-PPEEA$_{3500}$ were named as MP. The mixed micellar nano-particles were resuspended in DMEM culture medium containing 10 v/v % serum and the concentration of the mixed micellar nano-particles was 1 mg/ml.

Malvern ZetasizerNanao ZS90 dynamic light scattering spectrometer was used to detect the variation of the particle size of each of MP, MMP0.3, MMP0.6, MMP1 and MMP1.5 against time. Three repeated tests were done. Malvern Dispersion Technology Software 4.2 was used for the analysis and the average values were adopted. The relational graph between particle size and time was established (please see FIG. 4).

Figure 4:
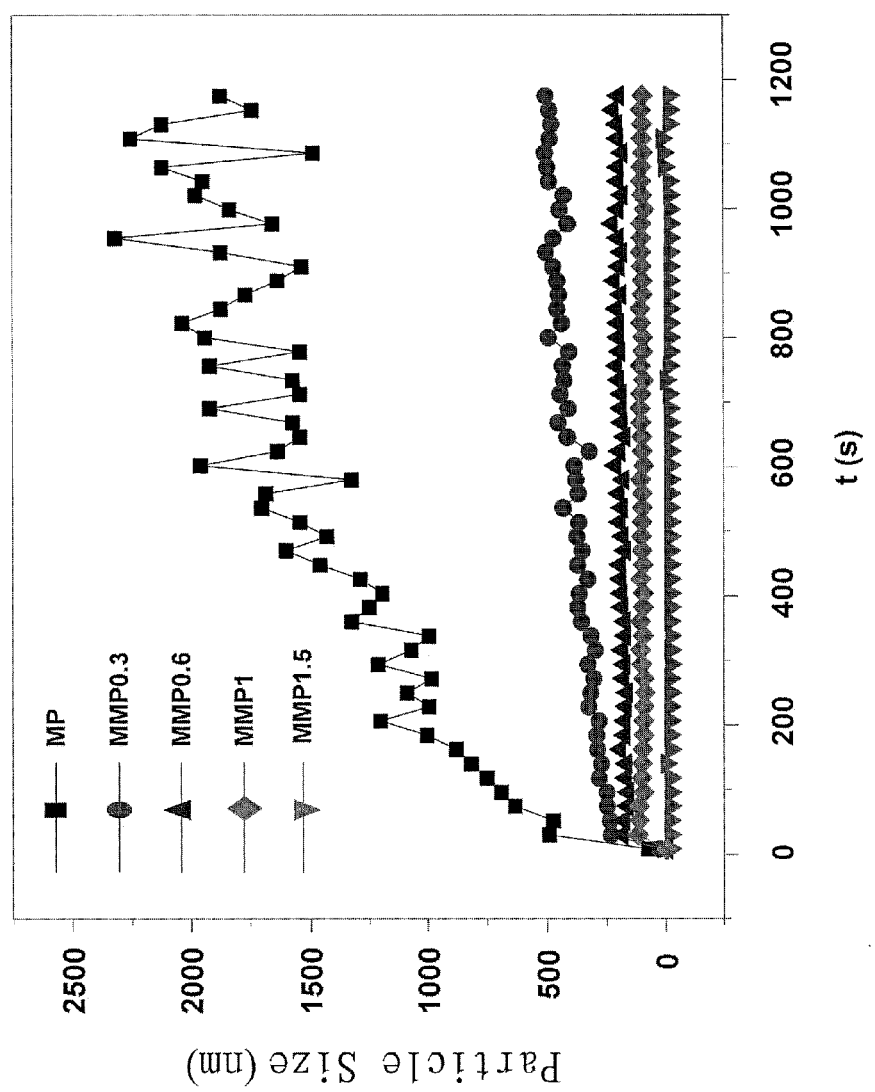
FIG. 4 is a variation trend chart of the particle size against the cultivation time when the mixed micelles prepared from $PCL_{3300}$-$PPEEA_{3500}$ and $PCL_{4400}$-$PEG_{2000}$ at different ratios cultivated in a culture medium containing 10% serum.

From FIG. 4, the micellar MP containing no $PCL_{4400}$-$PEG_{2000}$ was agglomerated quickly in the culture medium containing serum. As to the mixed micelles prepared from $PCL_{3300}$-$PPEEA_{3500}$ and $PCL_{4400}$-$PEG_{2000}$ at different ratios (see MMP0.3, MMP0.6, MMP1 and MMP1.5), they obviously improved the stability of the particles in the culture medium containing serum, and no agglomeration occurred during the long-time cultivation. The higher the portion of $PCL_{4400}$-$PEG_{2000}$ was, the more stable the mixed micelles were in serum and the less obvious the trend that the particle size increased with cultivation time was. Sequencing of the stability was MMP0.3<MMP0.6<MMP1<MMP1.5. That is, preparing mixed micellar nano-particles from $PCL_{3300}$-$PPEEA_{3500}$ and $PCL_{4400}$-$PEG_{2000}$ at different ratios and using them as vectors of nucleic acid preparation is a preferred embodiment of the present invention.

EXAMPLE 3

This example is intended to illustrate the performance evaluation of the mixed micellar nano-particles carrying CDK4 siRNA as a siRNA delivery system.

The following tests were conducted by using the mixed nano-particles prepared from $PCL_{4400}$-$PEG_{2000}$ and $PCL_{3300}$-$PPEEA_{3500}$ at a molar ratio of 1.5 in Example 2 which was named as MMP1.5.

(1) Influence of the Nucleic Acid Preparation Made from Mixed Micellar Nano-Particles MMP1.5 and siRNA on mRNA Expression of Endogenous Gene CDK4 of Lung Cancer Cells The siRNA (siCDK4) for CDK4 and the siRNA used as negative control were both provided by Shanghai GeneP-harma Co., Ltd. The positive-sense strand sequences of siRNAs were 5'-CAUCGUUCACCGAGAUCUGdTdT-3' (siCDK4, SEQ ID No: 1), 5'-AGUUCAACGACCAGUA-GUCdTdT-3'(negative control siRNA, SEQ ID No: 8); the antisense strand sequences were 5'-CAGAUCUCG-GUGAACGAUGdTdT-3'(siCDK4, SEQ ID No: 2), 5'-GACUACUGGUCGUUGAACUdTdT-3'(negative control siRNA, SEQ ID No: 10).

24 h after A549 cells (KRAS mutated lung cancer cell strain) and H661 cells (KRAS wild lung cancer cell strain) were inoculated in a six-well plate with density of $3 \times 10^5$/well, the cells were treated by the solutions of various vectors carrying or not carrying siCDK4. The volume of the mixed micellar nano-particle solution used in each group was 50 μl. After the treatment, the total volume of the liquid in each well was 2 ml. In each group, the vector, final concentration of the vector, type and final concentration of siRNA, and the molar ratio between amino in nano-particles and phosphate in nucleic acid (N/P) are shown in Table 6 below.

TABLE 6

| | Vector | Final concentration of the vector | Type and final concentration of siRNA (nM) | N/P |
|---|---|---|---|---|
| Treatment 1, control group | PBS | 25 μl/ml | — | — |
| Treatment 2, $Lipo_{siCDK4}$ | Lipofectamine 2000 | 2.5 μl/ml | siCDK4, 50 | — |
| Treatment 3, MMP1.5 | MMP1.5 | 36 μg/ml | — | — |
| Treatment 4, $MMP1.5_{siN.C.}$ | MMP1.5 | 36 μg/ml | siN.C., 200 | 5 |

TABLE 6-continued

| | Vector | Final concentration of the vector | Type and final concentration of siRNA (nM) | N/P |
|---|---|---|---|---|
| Treatment 5, $MMP1.5_{siCDK4}$ | MMP1.5 | 18 μg/ml | siCDK4, 100 | 5 |
| Treatment 6, $MMP1.5_{siCDK4}$ | MMP1.5 | 27 μg/ml | siCDK4, 150 | 5 |
| Treatment 7, $MMP1.5_{siCDK4}$ | MMP1.5 | 36 μg/ml | siCDK4, 200 | 5 |
| Treatment 8, MMP1.5 | MMP1.5 | 27 μg/ml | — | — |
| Treatment 9, $MMP1.5_{siN.C.}$ | MMP1.5 | 27 μg/ml | siN.C., 100 | 7.5 |
| Treatment 10, $MMP1.5_{siCDK4}$ | MMP1.5 | 27 μg/ml | siCDK4, 100 | 7.5 |
| Treatment 11, MMP1.5 | MMP1.5 | 36 μg/ml | — | — |
| Treatment 12, $MMP1.5_{siN.C.}$ | MMP1.5 | 36 μg/ml | siN.C., 100 | 10 |
| Treatment 13, $MMP1.5_{siCDK4}$ | MMP1.5 | 36 μg/ml | siCDK4, 100 | 10 |

After 24 h's transfection and cultivation, total RNA in the cells of each group were extracted with RNeasy mini-kits (Qiagen), the absorbances at $OD_{280}$ and $OD_{260}$ of the extracted RNA sample were determined by ultraviolet spectrophotometer, and the concentration of the RNA sample was calculated with Equation I: RNA concentration (μg/μL)=0.04×$OD_{260}$×dilution factor (Equation I). Then PrimeScript™ 1st Strand cDNA Synthesis Kit (Takara) was used to synthesize the first-strand cDNA. Each sample used 2 μg of total RNA. After synthesis of cDNA, PCR reaction was conducted according to the following reaction system (Takara). The reaction system included: 5 μl of 10×PCR Buffer (containing $MgCl_2$), 1 μl of dNTP mixture (200 mM), 1 μl of forward primer F1 (0.2 mM, the sequences were: 5'-ATC AAG AAG GTG GTG AAG CAG GCA-3' (GAPDH, SEQ ID No: 3), 5'-GCC TTC CCA TCA GCA CAG TTC-3'(CDK4, SEQ ID No: 4)), 1 μl of reverse primer R1 (0.2 mM, the sequences were: 5'-TGG AAG AGT GGG AGT TGC TGT TGA-3' (GAPDH, SEQ ID No: 5), 5'-CAA AGA TAC AGC CAA CAC TCC-3'(CDK4, SEQ ID No: 6)), 0.5 μl of Taq DNA polymerase (5 U/μl), 2 μl of cDNA, and 40.5 μl of sterilized distilled water was added for total volume of 50 μl.

PCR reaction conditions: with regard to GAPDH: 1) denaturation at 94° C. for 5 min; 2) denaturation at 94° C. for 30 s; 3) annealing at 57° C. for 30 s; 4) extension at 72° C. for 1 min; 20 cycles; 5) extension at 72° C. for 10 min; with regard to CDK4: 1) denaturation at 94° C. for 5 min; 2) denaturation at 94° C. for 30 s; 3) annealing at 57° C. for 30 s; 4) extension at 72° C. for 90 s; 22 cycles; 5) extension at 72° C. for 10 min.

Figure 5:
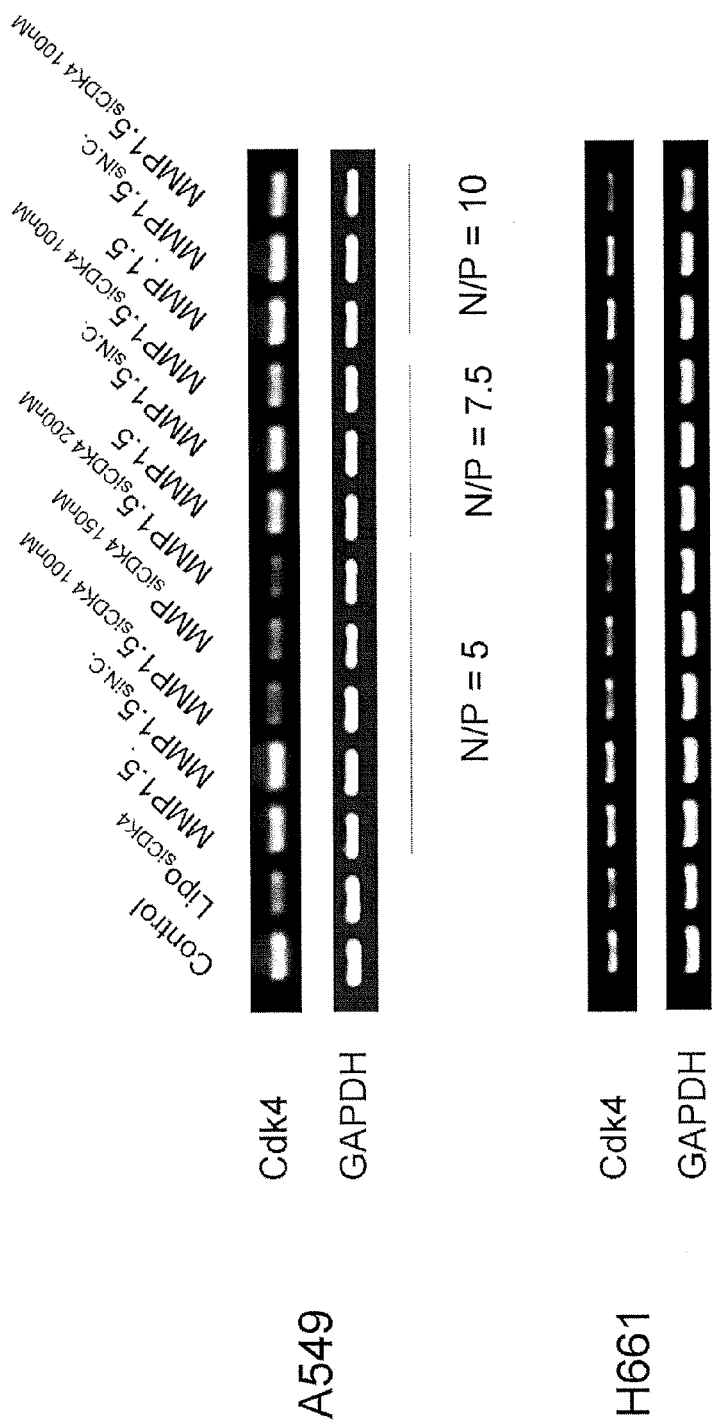
FIG. 5 shows the effect that siCDK4 carried by MMP1.5 silences the target gene in A549 and H661 lung cancer cells, respectively.

PCR product was tested by 1 wt % agarose gel electrophoresis. The result is shown in FIG. 5. In the control group, the expression level of CDK4 mRNA in the cells without siRNA treatment was very high. When N/P=5 and siCDK4 concentration was 100 nM, $MMP1.5_{siCDK4}$ could effectively silence the expression of CDK4, and with the increase of the dose of siCDK4, the silencing effect was enhanced. When N/P raised to 7.5 or 10, it could be observed that the expression level of CDK4 in the experimental group $MMP1.5_{siCDK4}$ decreased to some extent. The mixed micellar nano-particles binding siRNA at various N/P ratios could realize effective down-regulation of target gene CDK4. The CDK4 mRNA expression levels in the empty vector group of MMP1.5 and the group of $MMP1.5_{siN.C.}$ did not have significant difference from that in the control group (PBS), indicating the reduction of CDK4 mRNA expression level was specific and was not caused by the properties of nano-particles or siRNA.

(2) Influence of the Nucleic Acid Preparation Comprising Mixed Micellar Nano-Particles and siRNAs on Cycle of Lung Cancer Cells 24 hours after A549 cells and H661 cells were inoculated in a six-well plate with density of $3\times10^5$/well, the cells were treated with solutions of various vectors carrying or not carrying siCDK4. The volume of the mixed micellar nano-particle solution in each group was 50 μl. After the treatment, the total volume of the liquid in each well was 2 ml. In each group, the vector, final concentration of the vector, type and final concentration of siRNA, and N/P value are shown in Table 7 below.

TABLE 7

| | Vector | Final concentration of the vector | Type and final concentration of siRNA (nM) | N/P |
|---|---|---|---|---|
| Treatment 1, control group | PBS | 25 μl/ml | — | — |
| Treatment 2, Lipo$_{siCDK4}$ | Lipofectamine 2000 | 2.5 μl/ml | siCDK4, 50 | — |
| Treatment 3, MMP1.5 | MMP1.5 | 36 μg/ml | — | — |
| Treatment 4, MMP1.5$_{siN.C.}$ | MMP1.5 | 36 μg/ml | siN.C., 200 | 5 |
| Treatment 5, MMP1.5$_{siCDK4}$ | MMP1.5 | 18 μg/ml | siCDK4, 100 | 5 |
| Treatment 6, MMP1.5$_{siCDK4}$ | MMP1.5 | 36 μg/ml | siCDK4, 200 | 5 |

After 48 h's treatment, 0.25 wt % Trypsin-EDTA solution was used to digest the cells in each well. Then 2 ml of fresh culture medium was added to each well to terminate the reaction. The cells were collected to 10 ml centrifuge tube and centrifuged at 1000 rpm for 5 min, then were resuspended with PBS after the culture solution was removed, followed by being centrifuged at 1000 rpm for 5 min. After the centrifugation, the supernatant was removed. The cells in each tube were resuspended with 2 ml of 75 wt % ethanol (precooled at −40° C.) and kept in a refrigerator at 4° C. overnight. After ethanol transmembrane fixation, the solution was centrifuged at 1000 rpm for 5 min, the supernatant was removed and the remnant was washed with PBS twice. The cells in each tube were marked with 500 μl of dye solution (50 μg/ml PI, 100 μg/ml RNase A, 0.2% Triton X-100). After incubating in a dark place at 4° C. for 30 min, the samples were analyzed by a flow cytometer. The result is shown in FIG. 6.

Figure 6A:
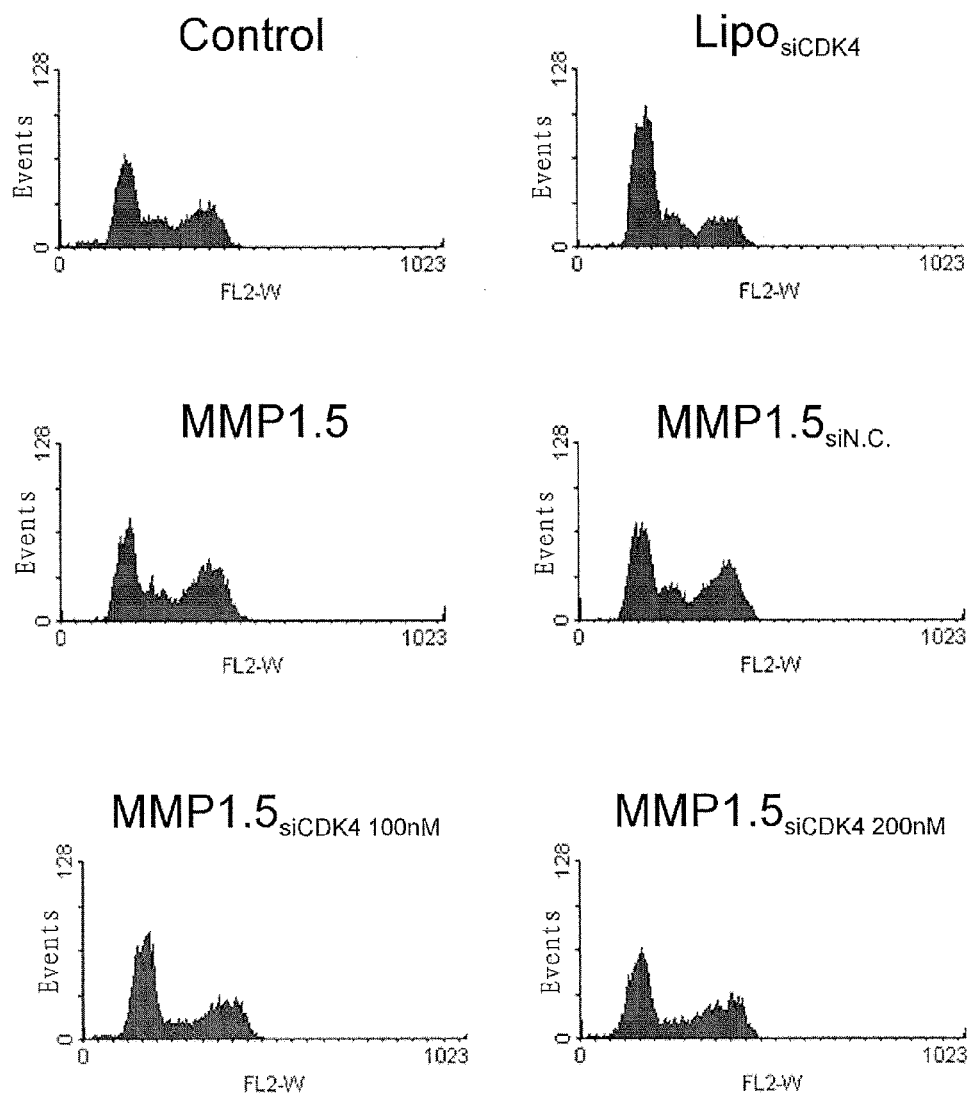
FIG. 6A shows the effect that siCDK4 carried by MMP1.5 retards cell cycle in A549 lung cancer cells.
Figure 6B:
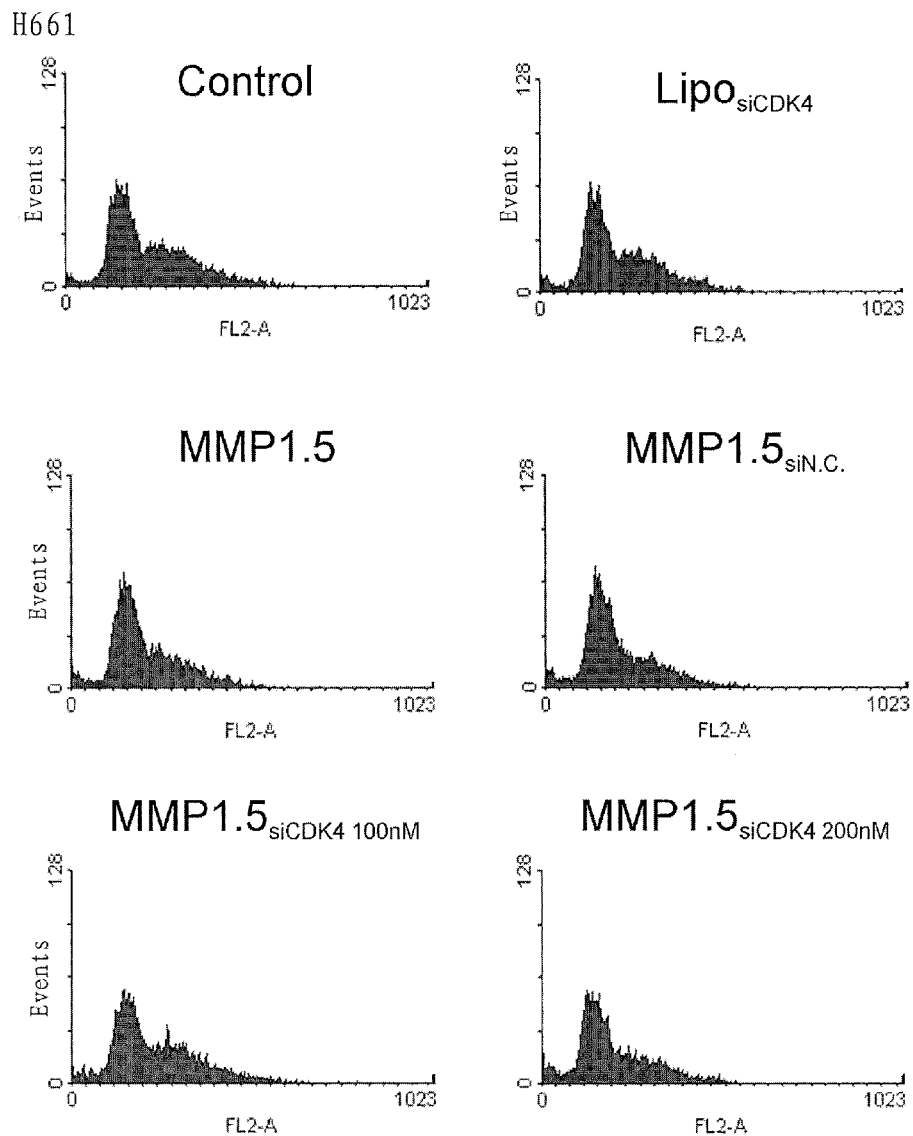
FIG. 6B shows the effect that siCDK4 carried by MMP1.5 retards cell cycle in H661 lung cancer cells.

FIG. 6 indicates that with regard to A549 cells, the cells from the groups treated with MMP1.5$_{siCDK4}$ and the positive control group of Lipo$_{siCDK4}$ mainly respectively stayed in stage G1, while the portions of the cells in stage G2 were small, the portions of the cells in stage S were obviously lower than that in the control group (PBS), and the cycle of the cells treated with MMP1.5 nano-particles or MMP1.5$_{siN.C.}$ did not change obviously. With regard to H661 cells, only silencing the expression of CDK4 didn't result in the change of cell cycle, as mainly reflected by the fact that the ratios in stages G1, G2 and S of the groups of MMP1.5$_{siCDK4}$ and the positive control group of Lipo$_{siCDK4}$ were not changed significantly.

(3) Influence of the Nucleic Acid Preparation Comprising Mixed Micellar Nano-Particles and siRNA on Proliferation of Lung Cancer Cells 24 h after A549 cells and H661 cells were inoculated in a 24-well plate with density of $7\times10^4$/well, the cells were treated with solutions of various vectors carrying or not carrying siCDK4, in which the volume of the mixed micellar nano-particle solution in each group was 50 μl. After the treatment, the total volume of the liquid in each well was 2 ml. The vector, final concentration of the vector, type and final concentration of siRNA, and N/P value of each group were shown in Table 8 below.

TABLE 8

| | Vector | Final concentration of the vector | Type and final concentration of siRNA (nM) | N/P |
|---|---|---|---|---|
| Treatment 1, control group | PBS | 25 μl/ml | — | — |
| Treatment 2, Lipo$_{siCDK4}$ | Lipofectamine 2000 | 2.5 μl/ml | siCDK4, 50 | — |
| Treatment 3, MMP1.5 | MMP1.5 | 36 μg/ml | — | — |
| Treatment 4, MMP1.5$_{siN.C.}$ | MMP1.5 | 36 μg/ml | siN.C., 200 | 5 |
| Treatment 5, MMP1.5$_{siCDK4}$ | MMP1.5 | 18 μg/ml | siCDK4, 100 | 5 |
| Treatment 6, MMP1.5$_{siCDK4}$ | MMP1.5 | 36 μg/ml | siCDK4, 200 | 5 |

After 72 h's treatment, 0.25 wt % Trypsin-EDTA solution was used to digest cells in each well. The groups were respectively inoculated in 6-well plates with density of 1000 cells per well and cultivated at 37° C. for 7 days. After washing with PBS and staining with crystal violet, the groups were photographed. The result was shown in FIG. 7.

Figure 7A:
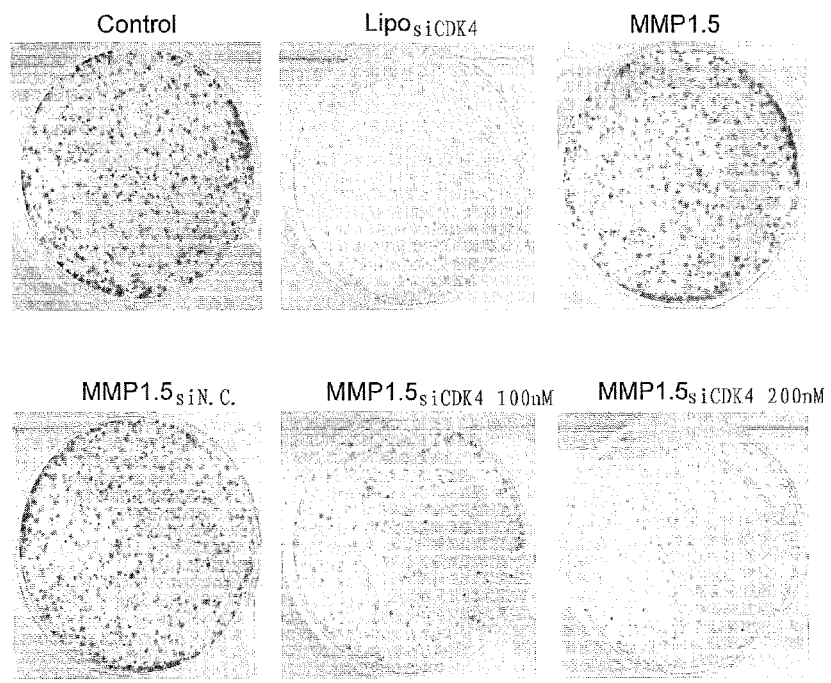
FIG. 7A shows the effect that siCDK4 carried by MMP1.5 inhibits cell clonality in A549 lung cancer cells.
Figure 7B:
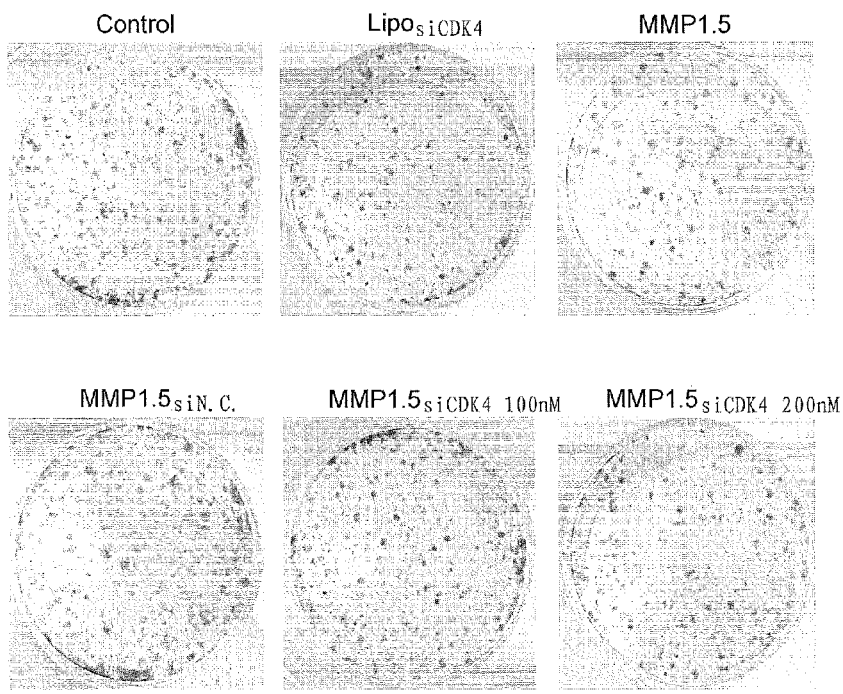
FIG. 7B shows the effect that siCDK4 carried by MMP1.5 inhibits cell clonality in H661 lung cancer cells.

FIG. 7 indicates that with regard to A549 cells, the cells of the control group (PBS) grew normally and formed plenty of clones; while in each of the groups treated with MMP1.5$_{siCDK4}$ and the positive control group of Lipo$_{siCDK4}$, the number of cell clones decreased obviously compared to the control group; after the cells were treated with MMP1.5 nano-particles or MMP1.5$_{siN.C.}$, the number of cell clones did not have significant difference compared to the control group. With regard to H661 cells, only silencing the expression of CDK4 did not result in reduction of the number of cell clones, and the number of cell clones in each of the groups of MMP1.5$_{siCDK4}$ and positive control group of Lipo$_{siCDK4}$ was equivalent to that in the control group.

EXAMPLE 4

This example is intended to illustrate the performance evaluation of the mixed micellar nano-particles carrying HIF-1α siRNA as a siRNA delivery system.

The following tests were conducted by using the mixed nano-particles prepared from PCL$_{4400}$-PEG$_{2000}$ and PCL$_{3300}$-PPEEA$_{3500}$ at a molar ratio of 1.5 in Example 2 which was named as MMP1.5.

(1) Influence of the Mixed Micellar Nano-Particles Delivering HIF-1α siRNA (siHIF) on Gene Expression in Lung Cancer Cells The siRNA for HIF-1α and the negative control siRNA were both provided by Shanghai GenePharma Co., Ltd. The positive-sense strand sequences were 5'-CGAUCAUGCA-GCUACUACAdTdT-3'(siHIF, SEQ ID No: 7), 5'-AGUU-CAACGACCAGUAGUCdTdT-3'(negative control siRNA, SEQ ID No: 8); the antisense strand sequences were 5'-UGUAGUAGCUGCAUGAUCGdTdT-3' (siHIF, SEQ ID No: 9), 5'-GACUACUGGUCGUUGAACUdTdT-3' (negative control siRNA, SEQ ID No: 10).

The silencing of HIF-1α mRNA in lung cancer cells by composite of MMP1.5 and HIF-1α siRNA was detected with the RT-PCR method to measure the expression level of HIF-1α mRNA in A549 cells which had been subjected tithe following treatment and cultivated for 24 h under simulated anoxic condition. The result is shown in FIG. 8.

Figure 8:
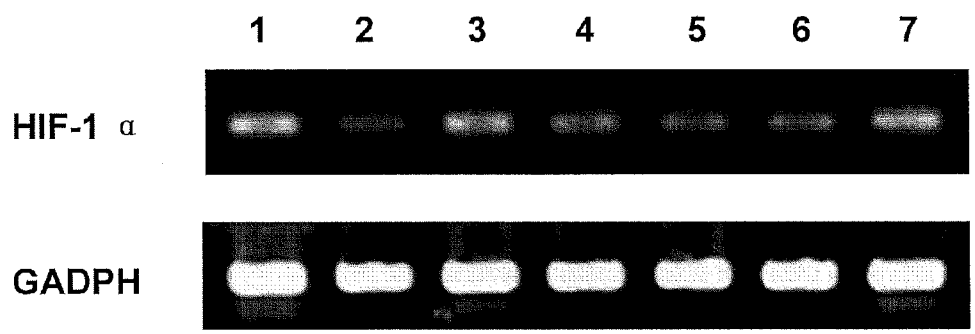
FIG. 8 shows the effect that siHIF carried by MMP1.5 micelles silences the target gene in A549 lung cancer cells.

From FIG. 8, MMPs/HIF-1α siRNA reduced the expression level of HIF-1α mRNA in A549 cells under simulated anoxic condition.

The treatment: A549 cells were inoculated in a 24-well plate with density of $3 \times 10^4$ cells/well, cultivated at 37° C. for 24 h, and treated with the solutions of various vectors carrying or not carrying siCDK4. The volume of the mixed micellar nano-particle solution used in each group was 50 μl. After the treatment, the total volume of the liquid in each well was 2 ml. The vector, final concentration of the vector, type and final concentration of siRNA, and N/P value in each group are shown in Table 9 below. A duplicate well was arranged in each treatment group.

TABLE 9

| | Vector | Final concentration of the vector | Type and final concentration of siRNA(nM) | N/P |
|---|---|---|---|---|
| Treatment 1, control group | PBS | 25 μl/ml | — | — |
| Treatment 2, Lipofectamine 2000 | Lipofectamine 2000 | 2.5 μl/ml | siHIF, 50 | — |
| Treatment 3, MMP1.5$_{siHIF}$ | MMP1.5 | 9 μg/ml | siHIF, 50 | 5 |
| Treatment 4, MMP1.5$_{siHIF}$ | MMP1.5 | 18 μg/ml | siHIF, 100 | 5 |
| Treatment 5, MMP1.5$_{siHIF}$ | MMP1.5 | 36 μg/ml | siHIF, 200 | 5 |
| Treatment 6, MMP1.5$_{siHIF}$ | MMP1.5 | 72 μg/ml | siHIF, 400 | 5 |
| Treatment 7, MMP1.5$_{siN.C.}$ | MMP1.5 | 72 μg/ml | siN.C., 400 | 5 |

CoCl$_2$ was added to the culture medium and its final concentration was 100 μM, so that the condition of anoxic culture was simulated. After 24 h's transfection and cultivation, the RNAiso Plus total RNA extraction kit (Takara) was used to extract total RNA in the cells of each group. The absorbances at OD$_{260}$ and OD$_{280}$ of the extracted RNA sample were determined by ultraviolet spectrophotometer, and the concentration of the RNA sample was calculated with Equation I. Then Reverse Transcriptase M-MLV (Takara) was used to synthesize the first strand of cDNA, and each sample used 1 μg of total RNA. After synthesis of cDNA, PCR reaction was conducted according to the following reaction system: 5 μl of 10×PCR Buffer (containing MgCl$_2$), 1 μl of 10 m MdNTP mixture, 1 μl of forward primer F2 (20 μM, the sequences were: 5'-ATC AAG AAG GTG GTG AAG CAG GCA-3' (GAPDH, SEQ ID No: 3), 5'-GCA AGC CCT GAA AGC G-3' (HIF-1α, SEQ ID No: 11)), 1 μl of reverse primer R2 (20 μM, the sequences were: 5'-TGG AAGAGT GGGAGT TGC TGT TGA-3' (GAPDH, SEQ ID No: 5), 5'-GGC TGT CCG ACT TTG A-3' (HIF-1α, SEQ ID No: 12)).

The PCR reactions: with regard to GAPDH, it was the same as above; with regard to HIF-1α: 1) denaturation at 94° C. for 5 min; 2) denaturation at 94° C. for 30 s; 3) annealing at 51° C. for 30 s; 4) extension at 72° C. for 30 s; 23 cycles; 5) extension at 72° C. for 10 min.

The PCR products were tested by 1 wt % agarose gel electrophoresis. The result indicated the expression level of HIF-1α mRNA in the cells of the control group without siRNA treatment was very high; the expression level of HIF-1α mRNA in the cells treated by positive control group of LiposiRNA reduced to some extent; and in the four groups in which siRNA was delivered by MMP1.5, all of the expression levels of HIF-1α mRNA in the cells reduced obviously as compared with the control group, moreover, when the concentration of siRNA raised from 50 nM to 100 nM, the expression level of HIF-1α mRNA reduced most obviously, and when the concentration of siRNA increased continuously, the silencing effect of HIF-1α mRNA did not increased obviously.

(2) Inhibitory Effect of the Mixed Micelles Delivering HIF-1α siRNA on Vascular Proliferation After transfection of prostate cancer cells by the composite of mixed micellar nano-particles and HIF-1α siRNA and the cells were cultivated for 24 h under simulated anoxic culture condition, the culture medium was used to detect its influence on angiogenesis of human umbilical cord endothelia cells HUVEC. The result is shown in FIG. 9.

Figure 9:
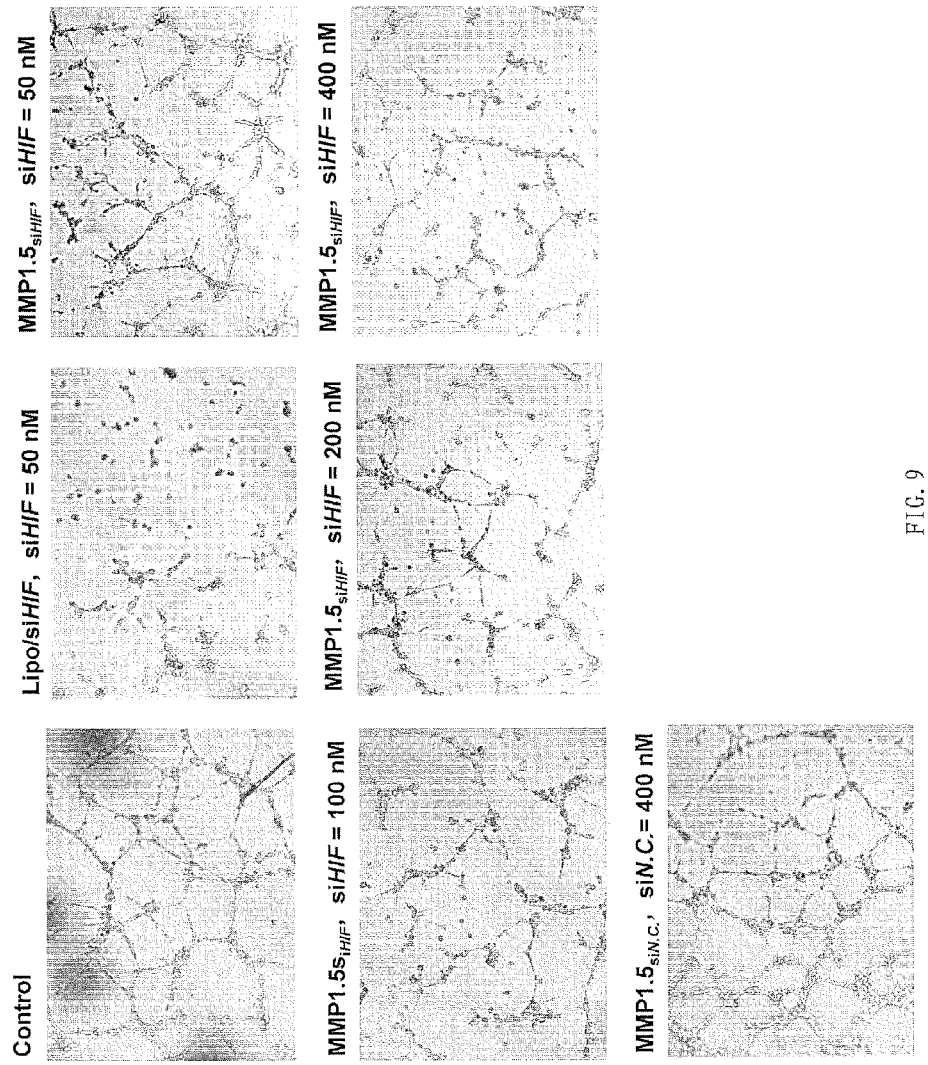
FIG. 9 shows the inhibition effect on the angiopoiesis ability of HUVEC vascular endothelial cells tested by the cell supernatant which was extracted from the PC3 prostate cancer cells 24 hours after being transfected with siHIF carried by MMP1.5.

From FIG. 9, under the simulated anoxic condition, the supernate of the culture medium of PC3 cell transfected by MMP1.5$_{siHIF}$ can inhibit HUVEC cells from forming vascular structure on Matrigel.

PC3 cells were inoculated in a 24-well plate with density of $5 \times 10^4$ cells/well, cultivated at 37° C. for 24 h and treated with solutions of various vectors carrying or not carrying siCDK4. The volume of the mixed micellar nano-particle solution used in each group was 50 μl. After the treatment, the total volume of the liquid in each well was 2 ml. The vector, final concentration of the vector, type and final concentration of siRNA, and N/P value are shown in Table 9. A duplicate well was arranged in each treatment group.

The culture medium for transfection was a DMEM/F12 culture medium containing 0.1 wt % BSA. CoCl$_2$ was added and its final concentration was 100 μM, so that the anoxic culture condition was simulated.

Matrigel was used to pave 96-well plates which were then stabilized at room temperature for more than 30 min. HUVEC cells were inoculated onto Matrigel. The density of the inoculation was $1 \times 10^4$ cells/well. The PC3 cell culture medium with different treatments of 24 h described above was added and cultivated at 37° C. for 6 h. The angiogenesis of HUVEC cells on Matrigel was photographed. Under the simulated anoxic condition, as HIF-1α protein was stabilized, expression and secretion of downstream VEGF protein were promoted and HUVEC cells formed an obvious reticular vascular structure on Matrigel. However, if the mixed micelles carrying HIF-1α siRNA were used to transfect PC3 cells, as the expression of HIF-1α was significantly down-regulated, the secretion of the regulated VEGF protein in the downstream decreased accordingly and the angiogenesis ability of HUVEC cells cultivated with the supernate of the cells was weakened obviously. When HIF-1α siRNA concentration was 50 nM, a few reticular structures were still observed. When siRNA concentration further raised to over 100 nM, only short and cracked tubulous structures were observed, suggesting HUVEC cells cannot form effective blood vessels without the protein secretory of the regulated VEGF in the downstream of HIF-1α.

(3) Inhibitory Effect of the Mixed Micellar Nano-Particles Delivering HIF-1α siRNA on Cell Migration After transfection of prostate cancer cells by the composite of mixed micellar nano-particles and HIF-1α siRNA and the cells were cultivated for 24 h under simulated anoxic culture condition, scratch removal method was used to detect its influence on cell migration ability. The result is shown in FIG. 10.

Figure 10:
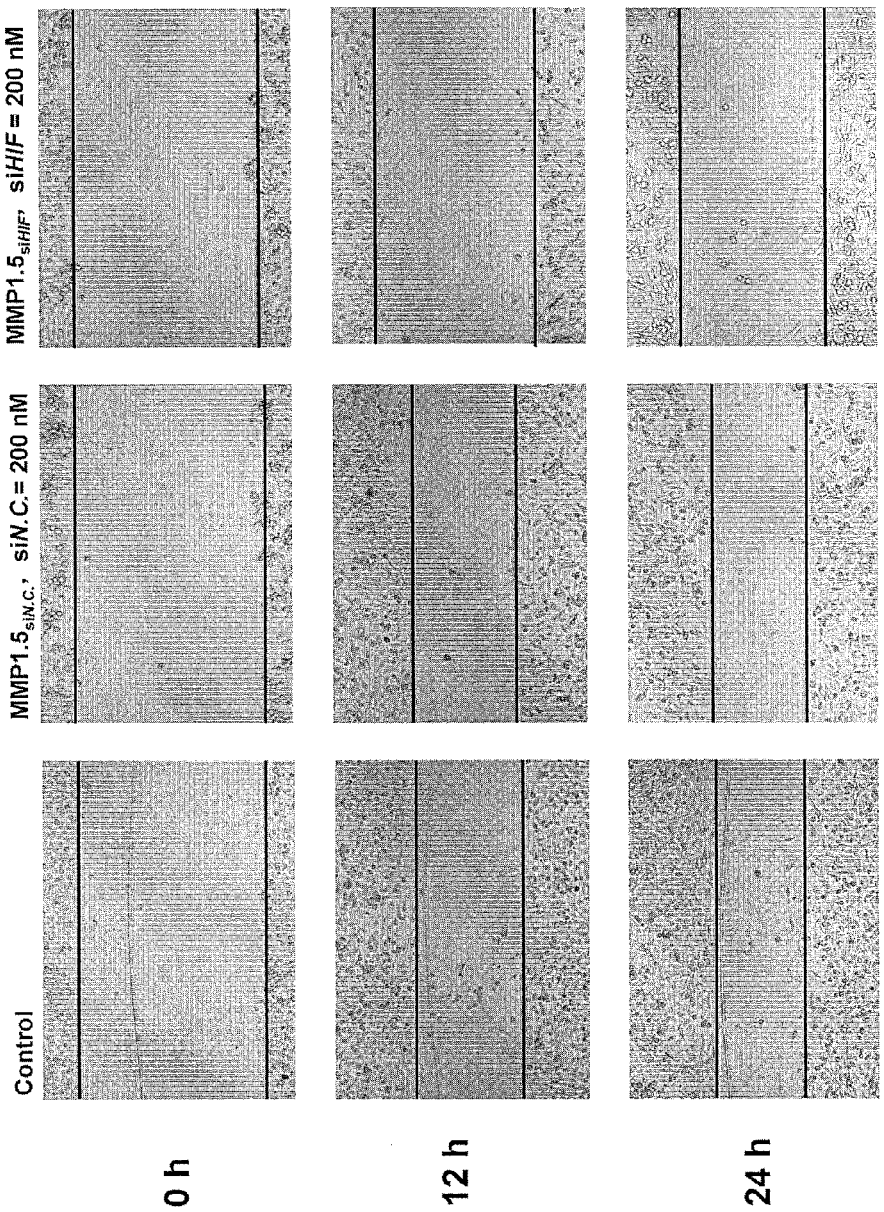
FIG. 10 shows the inhibition effect on cell migration ability determined by observing a scar scratched on the cellular layer of the PC3 prostate cancer cells after transfected with siHIF carried by MMP1.5.

FIG. 10 indicates that the cell migration ability was inhibited after PC3 cells were transfected by MMP1.5$_{siHIF}$ under simulated anoxic condition.

PC3 cells were inoculated in a 24-well plate with density of $5\times10^4$ cells/well, cultivated at 37° C. for 24 h and treated with solutions of various vectors carrying or not carrying siCDK4. The volume of the mixed micellar nano-particle solution used in each group was 50 μl. After the treatment, the total volume of the liquid in each well was 2 ml. The vector, final concentration of the vector, type and final concentration of siRNA, and N/P value in each group were shown in Table 10. A duplicate well was arranged in each treatment group.

TABLE 10

| | Vector | Final concentration of the vector | Type and final concentration of siRNA (nM) | N/P |
|---|---|---|---|---|
| Treatment 1, control group | PBS | 25 μl/ml | — | — |
| Treatment 2, MMP1.5$_{siN.C.}$ | MMP1.5 | 36 μg/ml | siHIF, 200 | 5 |
| Treatment 3, MMP1.5$_{siN.C.}$ | MMP1.5 | 36 μg/ml | siN.C., 200 | 5 |

CoCl$_2$ was added to DMEM/F12 culture medium and its final concentration was 100 μM, so that the anoxic culture condition was simulated. After 24 h's transfection and cultivation, a scar was scratched on the cell layer by a 1 ml pipette tip. The cells were continuously cultivated for 12 h and 24 h respectively in a culture medium under the simulated anoxic condition, and the cell migration effect was respectively observed by photographing. Under the simulated anoxic condition, HIF-1α in the control group and the negative control group were effectively stabilized. In the group of HIF-1α siRNA, as HIF-1α mRNA was silenced, the protein content of HIF-1α was lower than other groups. Therefore, the effect that HIF-1α as an important transcriptional regulation factor promotes tumor growth under the anoxic condition was not reflected, and the healing effect of the "scar" was much poorer.

EXAMPLE 5

This example is intended to illustrate that the mixed micellar nano-particles modified by acetyl galactose were used as liver siRNA vector to silence the expression of endogenous gene of the liver.

PEG$_{2000}$ terminals on the surface of the mixed nano-particles prepared from PCL$_{4400}$-PEG$_{2000}$ and PCL$_{3300}$-PPEEA$_{3500}$ at a molar ratio of 1.5 in Example 2 which was named as MMP1.5 were respectively modified with acetyl galactose and glucose and named as GalNAc-MMP1.5 and Glu-MMP1.5 for the following tests.

(1) the Nucleic Acid Preparation of the Mixed Micellar Nano-Particles Modified by Acetyl Galactose and siRNA Targeted Parenchymal Hepatic Cells In Vitro Parenchymal hepatic cells were perfusion separated and inoculated in a 24-well plate with density of $5\times10^4$ cells/well. After 24 h's cultivation at 37° C., an endocytosis test was done. The parenchymal hepatic cells were respectively incubated with the FAM-siRNA-carrying mixed micelles of GalNAc-MMP1.5 and Glu-MMP1.5 at 37° C. for 1 h, then washed with PBS twice. A flow cytometer (FACS, BD Bioscience, Bedford, Mass.) was used to determine fluorescence intensity of FAM in the cells of each group.

In the competitive inhibition test, before adding GalNAc-MMP1.5 and Glu-MMP1.5, galactosamine (with final concentration of 60 mM) was pre-combined with the parenchymal hepatic cells for 1 h. Other operations were the same as above.

Figure 11:
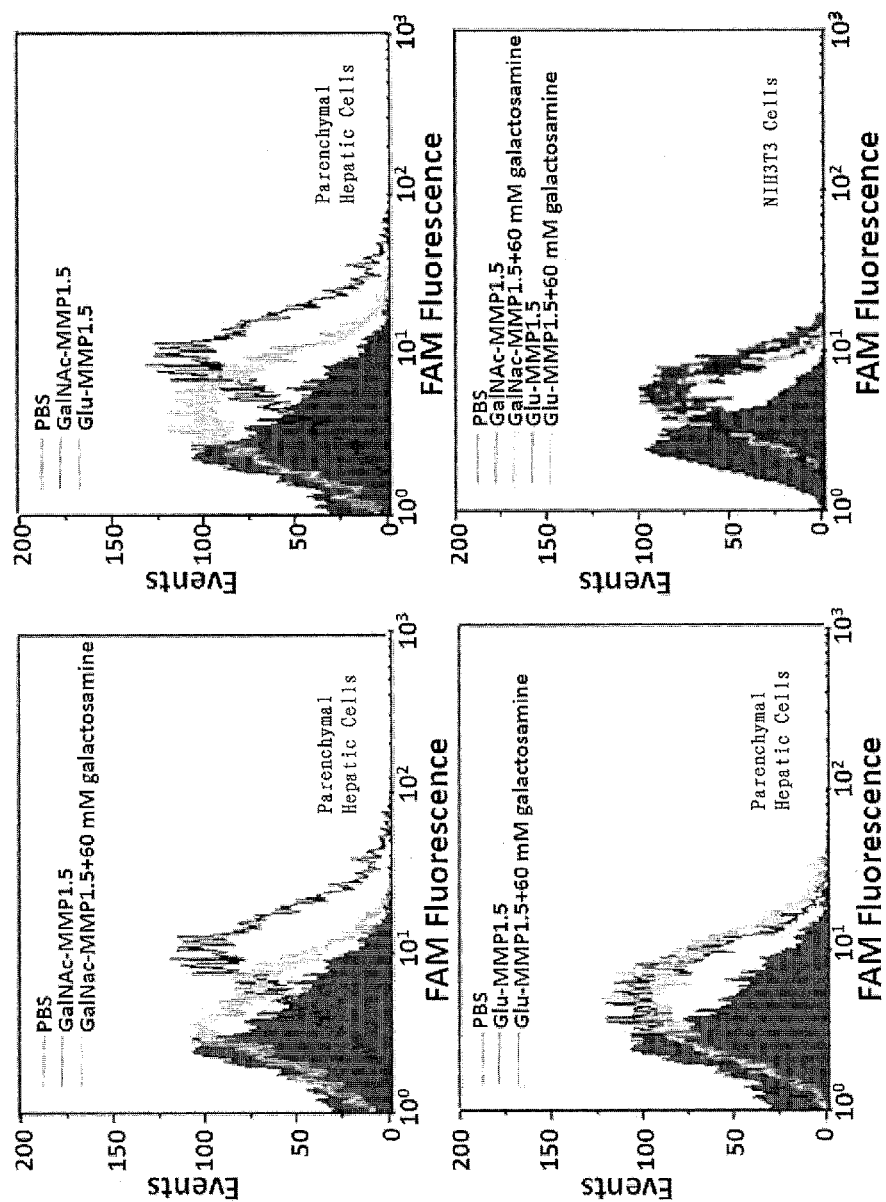
FIG. 11 shows the endocytosis effects of parenchymal hepatic cells and NIH3T3 cells on acetyl galactose modified mixed nano-micelles (GalNAc-MMP1.5) and glucose modified mixed nano-micelles (Glu-MMP1.5) which were respectively bound with FAM-siRNA detected by a flow cytometer.

The result is shown in FIG. 11. Compared with the control group and the Glu-MMP1.5 group, the fluorescence intensity in the cells of the GalNAc-MMP1.5 group was the highest. This suggests that modification of acetyl galactose on the surface of the mixed micellar nano-particles can promote the particles to carry more siRNA into the parenchymal hepatic cells, while in the non-liver cell line NIH3T3, such difference doesn't appear. Regarding the culture medium containing 60 mM galactosamine, the amount of GalNAc-MMP1.5 entering the parenchymal hepatic cells was inhibited obviously, suggesting that the targeting advantage of the particles relies on the specific endocytosis mediated by asialogalactose receptor.

(2) the Nucleic Acid Preparation of the Mixed Micellar Nano-Particles Modified by Acetyl Galactose and siRNA has the Ability to Silence Liver Hepatic Endogenous Gene In Vitro Apolipoprotein B is a protein specifically expressed and extracellularly secreted by hepatic cells. By silencing the expression of this protein, the ability of the liver-targeted nucleic acid preparation of the mixed micellar nano-particles and siRNA to silence gene was detected.

The siRNA for ApoB and siRNA of the negative control group were both provided by Suzhou Ribo Life Science Co., Ltd. The positive-sense strand sequences were 5'-GUfC-fAUfCfACACUGAAUACfCfAAUfdTdT-3' (siRNA for ApoB, SEQ ID No: 13) and 5'-UmUCmUCmCGAACGUG-mUCmAmCGUdTdT-3' (negative control group, SEQ ID No: 14) respectively; and the antisense strand sequences were 5'-pAUfUfGGUAUUCAGUGUGAUfGACfACdTdT-3' (siRNA for ApoB, SEQ ID No: 15) and 5'-ACmGUf-GACfACGUUCfGGAGAAdTdT-3' (negative control group, SEQ ID No: 16) respectively.

Primary parenchymal hepatic cells were inoculated in a 24-well plate with density of $5\times10^4$ cells/well, cultivated at 37° C. for 24 h and treated with solutions of various vectors carrying or not carrying siCDK4. The volume of the mixed micellar nano-particle solution used in each group was 50 μl. After the treatment, the total volume of the liquid in each well was 2 ml. The vector, final concentration of the vector, type and final concentration of siRNA, and N/P value in each group are shown in Table 11. A duplicate well was arranged in each treatment group.

TABLE 11

| | Vector | Final concentration of the vector | Type and final concentration of siRNA (nM) | N/P |
|---|---|---|---|---|
| Treatment 1, control group | PBS | 25 μl/ml | — | — |
| Treatment 2, free siApoB | siApoB solution | 25 μl/ml | 400 | — |

TABLE 11-continued

| Vector | | Final concentration of the vector | Type and final concentration of siRNA (nM) | N/P |
|---|---|---|---|---|
| Treatment 3, Lipofectamine 2000 | Lipofectamine 2000 | 1.25 µl | siCDK4, 50 | — |
| Treatment 4, GalNAc-MMP1.5$_{siN.C.}$ | MMP1.5 | 72 µg/ml | siN.C., 400 | 5 |
| Treatment 5, GalNAc-MMP1.5$_{siApoB}$ | MMP1.5 | 72 µg/ml | siApoB, 400 | 5 |
| Treatment 6, Glu-MMP1.5$_{siApoB}$ | MMP1.5 | 72 µg/ml | siApoB, 400 | 5 |

After 24 h's transfection and cultivation, the RNAiso Plustotal RNA extraction kit (Takara) was used to extract the total RNA in the cells of each group. The absorbances at $OD_{280}$ and $OD_{260}$ of the extracted RNA sample were determined by ultraviolet spectrophotometer, and the concentration of the RNA sample was calculated with Equation I. Then Reverse Transcriptase M-MLV (RNase H⁻) (TaKaRa) was used to synthesize the first strand of cDNA. Each sample used 2 µg of the total RNA. After synthesis of cDNA, RealMasterMix (SYBR Green) was used for three-step fluorogenic quantitative PCR, set GAPDH as an internal reference to normalize cDNA.

Primers of the Fluorogenic Quantitative PCR:

```
GAPDH:
Forward primer:
                            (SEQ ID No: 3)
5'-ATCAAGAAGGTGGTGAAGCAGGCA-3'

Reverse primer:
                            (SEQ ID No: 5)
5'-TGGAAGAGTGGGAGTTGCTGTTGA-3'

ApoB:
Forward primer:
                            (SEQ ID No: 17)
5'-TTCCAGCCATGGGCAACTTTACCT-3'

Reverse primer:
                            (SEQ ID No: 18)
5'-TACTGCAGGGCGTCAGTGACAAAT-3'
```

Reaction of the fluorogenic quantitative PCR: 1) denaturation at 94° C. for 1 min; 2) denaturation at 94° C. for 15 s; 3) annealing at 59° C. for 15 s; 4) extension at 68° C. for 1 min; 40 cycles.

Figure 12:
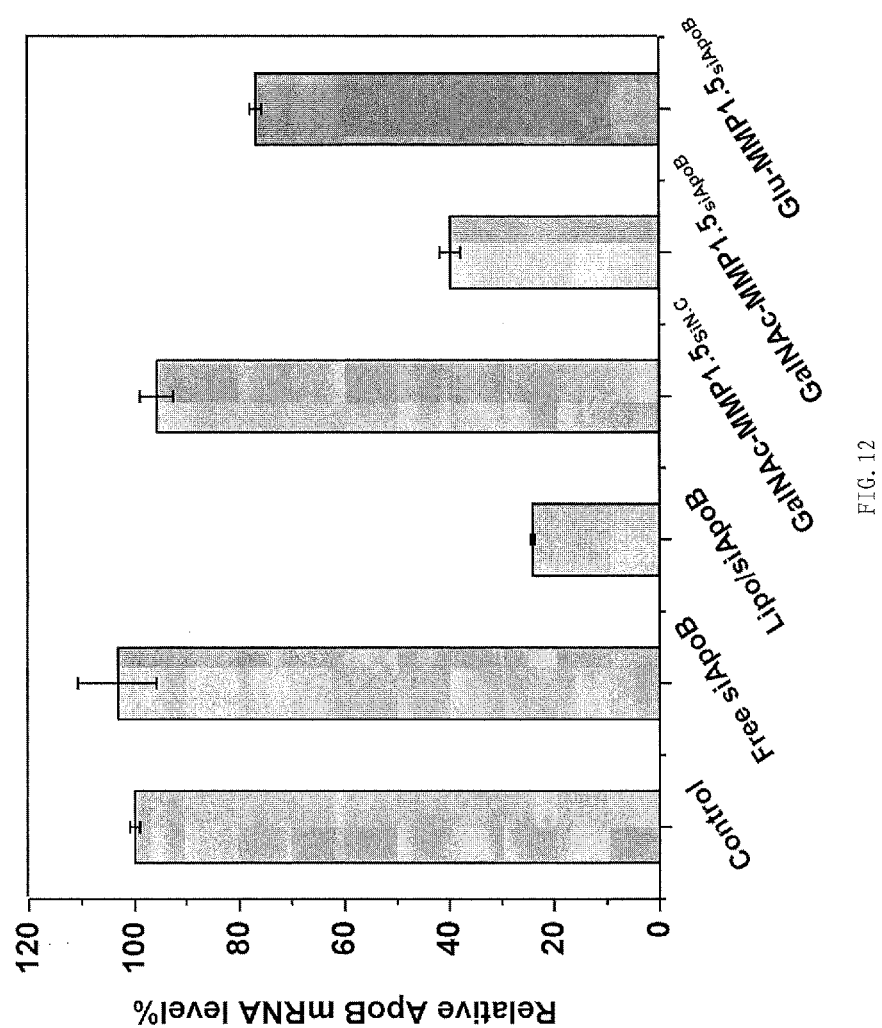
FIG. 12 shows the effects that siApoB carried by different nano-micelle particles silences the target gene in parenchymal hepatic cells.

According to the result of FIG. 12, the expression levels of ApoBin the cells from the control group, free siApoB treatment group and GalNAc-MMP1.5$_{siN.C.}$ group were very high, while the expression level of ApoB mRNA in the cells treated by Lipofectamine 2000 reduced to some extent. In addition, the expression level of ApoB mRNA in GalNAc-MMP1.5$_{siApoB}$ cells reduced obviously as compared with the control groups and was even lower than the expression level of ApoB mRNA in the cells of the Glu-MMP1.5$_{siApoB}$ group. This suggests that the mixed nano-micellar siRNA composite modified by acetyl galactose can efficiently and specifically silence gene expression in parenchymal hepatic cells, and has the advantage of liver targeting.

(3) the Nucleic Acid Preparation of the Mixed Micellar Nano-Particles Modified by Acetyl Galactose and siRNA Targeted Parenchymal Hepatic Cells In Vivo 7~8-weeks old Balb/c mice (male) were respectively treated in the following way:

1) 200 µl of sterile PBS (pH=7.4) was injected via caudal vein; 2) 200 µl of free Cy5-siRNA isosmotic solution was injected via caudal vein, in which the action concentration of Cy5-siRNA was 2 mg/kg; 3) 200 µl of Glu-MMP1.5$_{Cy5-siRNA}$ isosmotic solution was injected via caudal vein, in which the action concentration of Cy5-siRNA was 2 mg/kg; 4) 200 µl of GalNAc-MMP1.5$_{Cy5-siRNA}$ isosmotic solution was injected via caudal vein, in which the action concentration of Cy5-siRNA was 2 mg/kg.

12 h later, the mice were killed by avascularization. Their visceral organs were taken and observed under fluorescence. After fixed with 4 wt % paraformaldehyde (pH=7.4), the livers were sectioned, and the fluorescence distribution of the interior tissue of the livers were observed under laser scanning confocal microscope.

Figure 13A:
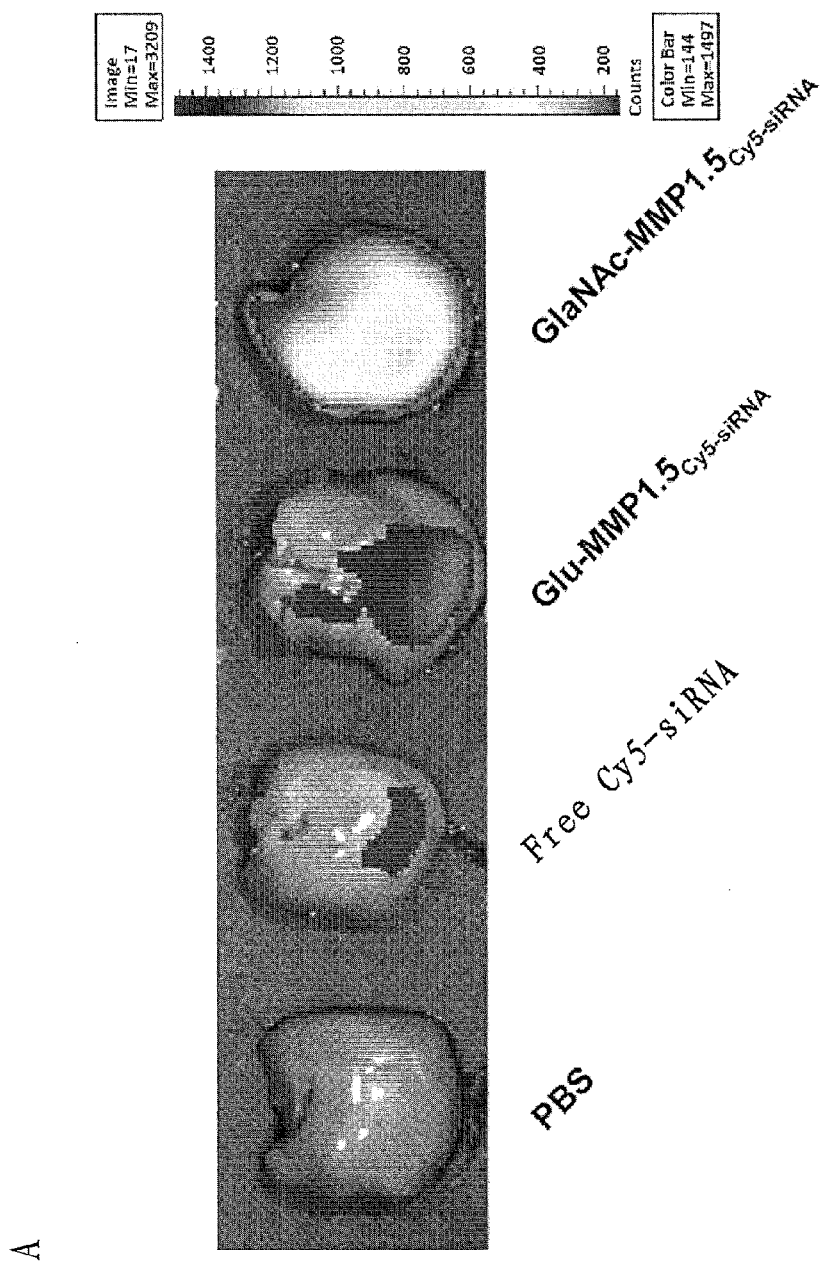
FIG. 13A shows the result of the nano-micelle particles enriched in liver after injecting PBS, free Cy5-siRNA, Glu-MMP1.5$_{Cy5-siRNA}$ and GalNAc-MMP1.5$_{Cy5-siRNA}$ via caudal vein of the mice.
Figure 13B:
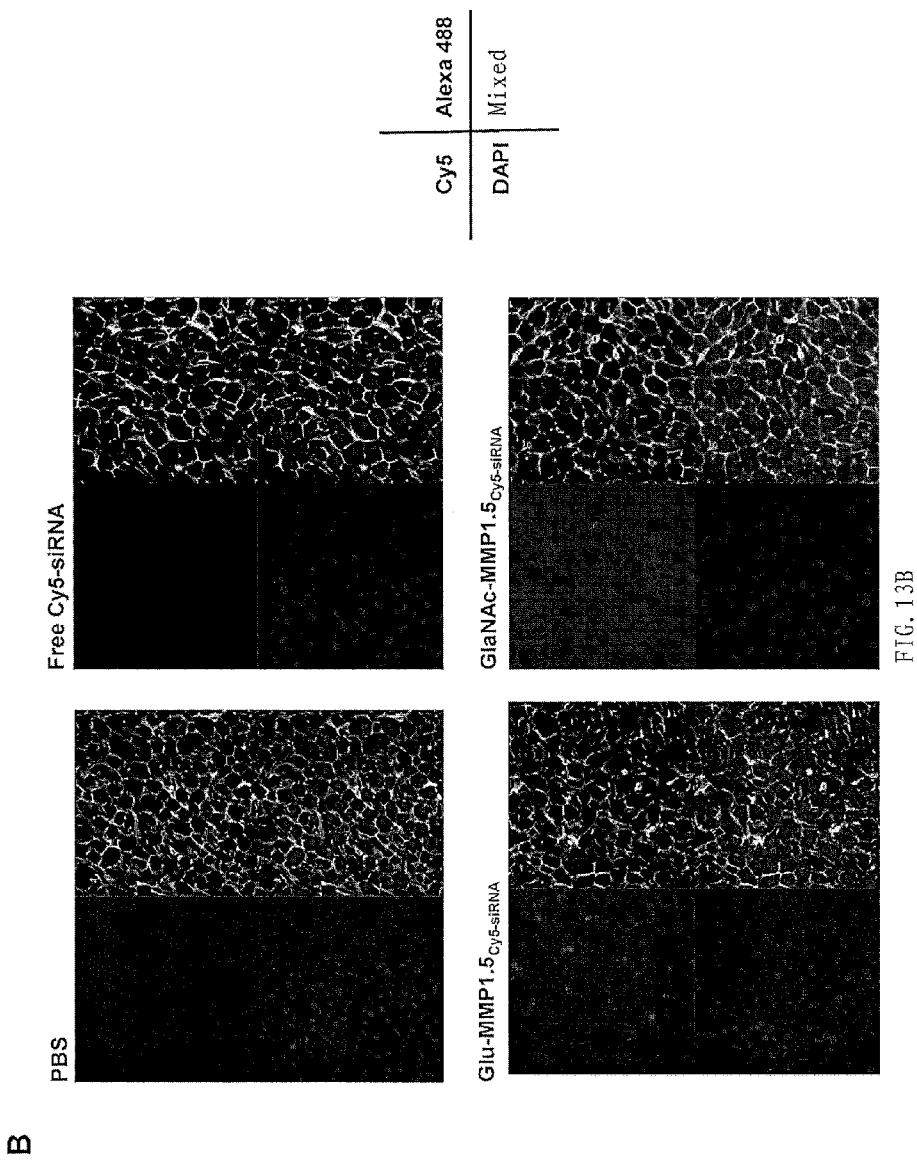
FIG. 13B shows the result of the micellar nano-particles entering parenchymal hepatic cells by biopsy of liver.

The experimental result is shown in FIG. 13A. Comparing the fluorescence intensities of brains, hearts, lungs, livers, kidneys and spleens of the mice in each group, almost all the Cy5-siRNAs from the free Cy5-siRNA group and the Glu-MMP1.5$_{Cy5-siRNA}$ group were removed through kidneys, while in the GalNAc-MMP1.5$_{Cy5-siRNA}$ group, it showed much fluorescence retention in livers. In the later observation of the fluorescence distributions of internal liver under the fluorescence microscope after the liver tissues were sectioned, the fluorescence of the GalNAc-MMP1.5$_{Cy5-siRNA}$ group was evenly distributed in various kinds of cells of the liver, while no fluorescence was observed in either the control group or the free Cy5-siRNA group, and much more of the fluorescence in the Glu-MMP1.5$_{Cy5-siRNA}$ group existed in Kupffer cells, rather than in parenchymal hepatic cells. The result is shown in FIG. 13B. This experiment confirms the mixed micellar nano-particles of GalNAc-MMP1.5 modified by galactose can effectively target liver and has the ability of in vivo application.

(4) the Nucleic Acid Preparation of the Mixed Micellar Nano-Particles Modified by Acetyl Galactose and siRNA has an Ability to Silence Hepatic Endogenous Gene In Vivo The potential for in vivo application with regard to liver-targeted composite of the mixed nano-micelles and siRNA was observed by silencing the expression of hepatic endogenous protein ApoB by administering via the venous system. 7~8 weeks old Balb/c mice (male) were selected. Each group had six mice which were respectively treated in the following way. Drugs were administered every other day, in total five times.

1) 400 µl of sterile 5% glucose buffer solution (pH=7.4) was injected via caudal vein; 2) 400 µl of free siApoB isosmotic solution was injected via caudal vein, in which the dose of siApoB was 8 mg/kg; 3) 2 ml of siApoB isosmotic solution was injected with high pressure via caudal vein, in which the action concentration of siApoB was 40 mg/kg, it was injected only once and the mice were killed after 48 h, and the detections of other indicators were the same as other groups; 4) 400 µl of GalNAc-MMP1.5 isosmotic solution was injected via caudal vein, in which the concentration of GalNAc-MMP1.5 was the same as that in Group 5 and Group 6; 5) 400 µl of GalNAc-MMP1.5$_{siN.C.}$ isosmotic solution was injected via caudal vein, in which the action concentration of siN.C. was 8 mg/kg; 6) 400 µl of GalNAc-MMP1.5$_{siApoB}$ isosmotic solution was injected via caudal vein, in which the action concentration of siApoB was 8 mg/kg; 7) 400 µl of Glu-MMP1.5$_{siApoB}$ isosmotic solution was injected via caudal vein, in which the action concentration of siApoB was 8 mg/kg.

48 h after the last administration, the mice were killed by avascularization. The livers were taken out and ground. The RNAiso total RNA extraction kit (TaKaRa) was used to extract total RNA in cells. The content of ApoB was detected by reverse transcription and fluorescence quantitative PCR (the same steps as those for detecting ApoB content in vitro in Example 5).

Figure 14:
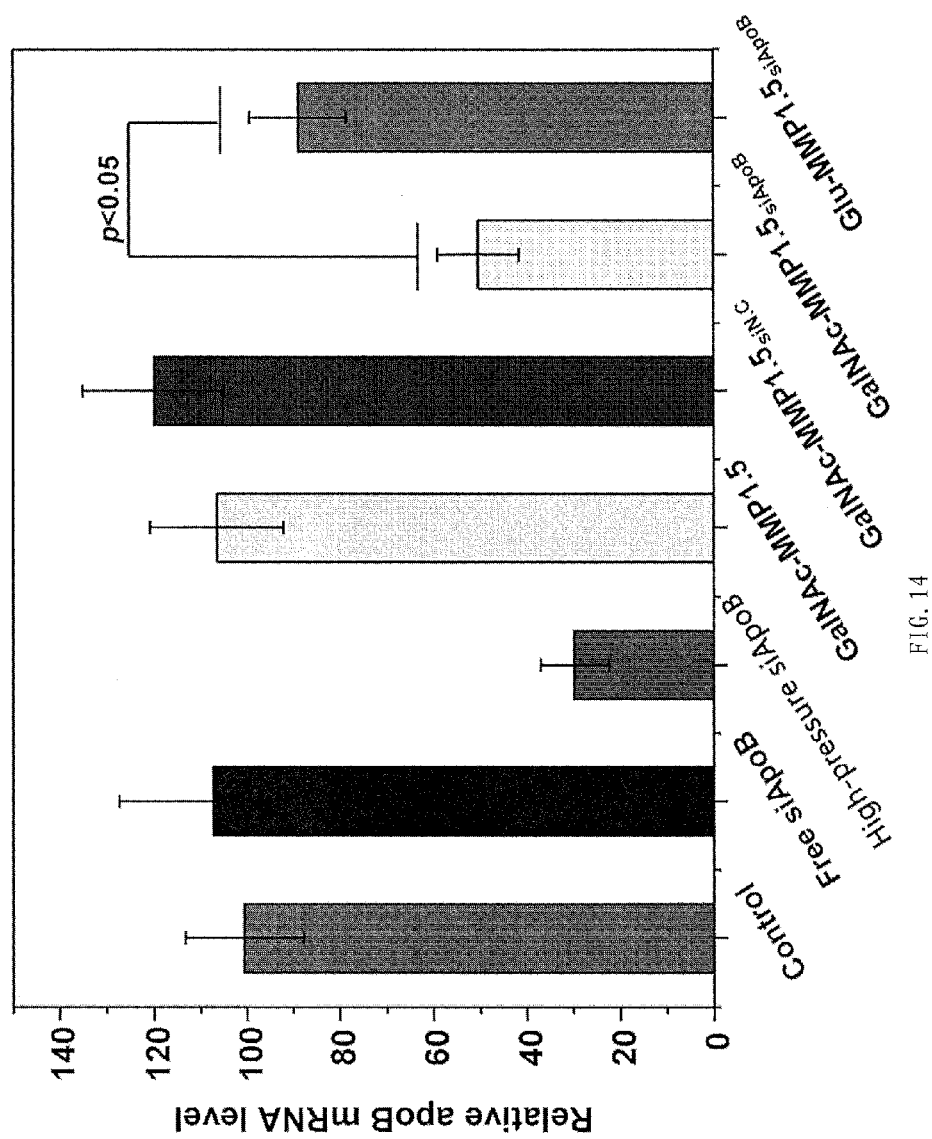
FIG. 14 shows the effect of the target gene in liver silenced by siApoB bound with different nano-micelle particles which was injected into mice via caudal vein five times.

In FIG. 14, the variations of ApoB mRNA expression in the mice's livers in each group after administration are shown. The expression level of ApoB mRNA in the positive control group with high-pressure intravenous injection decreased obviously. The expression level of ApoB mRNA in the GalNAc-MMP1.5$_{siApoB}$ group decreased significantly, and the silencing efficiency was as high as 49.6%, while the non-targeting nano-particles siApoB composite group decreased the expression level only by 11.2%. This suggests that the targeting modified nano-micelles can carry siRNA into parenchymal hepatic cells more efficiently to downregulate expression of target gene under the action of RNAi, therefore, it is a good liver siRNA delivery system, and has a huge application potential in treating liver diseases in future.

Further, the embodiments of the present invention may be freely combined, as long as they don't go against the idea of the present invention, which are also the content disclosed by the present invention.

COMPARISON EXAMPLE 1

This comparison example is intended to illustrate that the physical properties of the mixed micellar nano-particles can be adjusted and controlled by adjusting the constitution and the contents of the components in the mixture system containing PCL-PPEEA and PCL-PEG.

(1) Preparation of 3-Component Mixed Micellar Particles

The molar ratio between two block copolymers PCL$_{3300}$-PPEEA$_{3500}$ and PCL$_{4400}$-PEG$_{2000}$ was fixed at 1:1.5, and PCL$_{3900}$ was added to form a 3-component mixture system. The particular method for preparing the micellar particles from this 3-component mixture system was as follows. The above three polymers were mixed at the molar ratio shown in Table 12 below and dissolved in an organic solvent of acetonitrile:methanol=1:1. The solution was dropwise added into ultrapure water (1 mg/ml) under stirring. After a half hour's stirring, it was dialyzed for 5 h in a dialysis bag (molecular weight cutoff of 2 k) to remove the organic solvent.

(2) Measurement of the Particle Size and Zeta Potential of the 3-Component Mixed Micellar Particles The foregoing solution of 3-component mixed micellar particles was diluted with ultrapure water to 0.1 mg/ml. The particle size and surface potential of the obtained particles were measured by Malvern ZetasizerNano ZS90 dynamic light scattering spectrometer. The result is shown in Table 12.

TABLE 12

| | mPEG-PCL:PCL:PCL-PPEEA (Molar ratio) | Particle size (nm) | Potential (mV) |
|---|---|---|---|
| MNP-40 | 1.5:0:1 | 36.83 ± 3.86 | 33.5 ± 2.0 |
| MNP-90 | 1.5:3.5:1 | 90.19 ± 1.28 | 59.4 ± 2.8 |
| MNP-150 | 1.5:6.4:1 | 150.10 ± 1.35 | 63.5 ± 1.2 |
| MNP-220 | 1.5:15.9:1 | 221.06 ± 4.30 | 64.6 ± 0.9 |
| MNP-290 | 1.5:36.6:1 | 287.76 ± 15.03 | 68.4 ± 0.4 |

Figure 15:
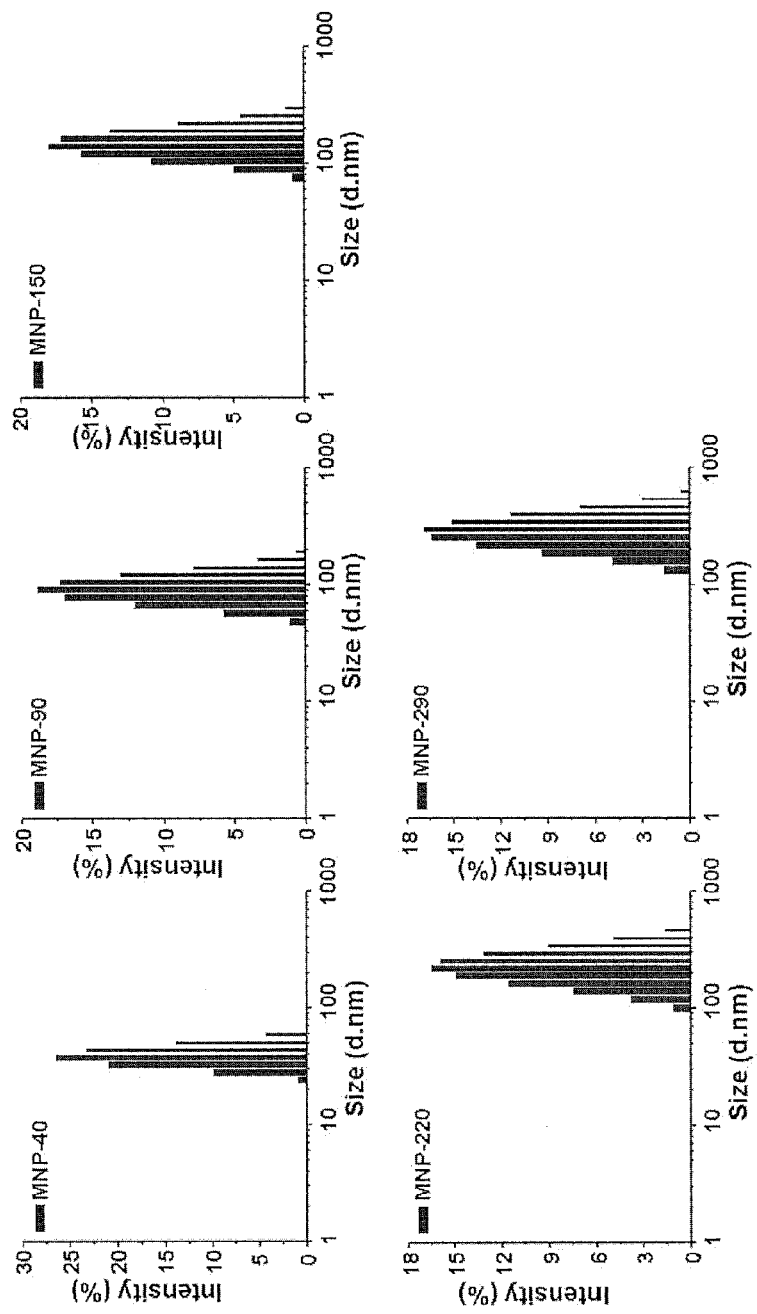
FIG. 15 shows the particle size distribution of the mixed micellar particles consisting of three components: $PCL_{3300}$-$PPEEA_{3500}$, $PCL_{4400}$-$PEG_{2000}$ and $PCL_{3900}$.

From Table 12, the particle size of the micellar particles increased with the increase of the content of PCL$_{3900}$ in the 3-component mixture system. Finally, the micellar particles of 40, 90, 150, 220 and 290 nm were obtained and named as MNP-40, MNP-90, MNP-150, MNP-220 and MNP-290 respectively. Further, according to the particle distribution data in Table 12 and FIG. 15, the mixed micellar particles of MNP-40, MNP-90, MNP-150, MNP-220 and MNP-290 had small dispersity of particle size and have good uniformity. The surface potential of these particles varied with the addition and content of PCL$_{3900}$ component in the 3-component mixture system (increased from 33.5±2.0 mV to 68.4±0.4 mV). The above result indicates the particle size, surface potential and other physical properties of the mixed micellar particles provided by the present invention can be controlled by regulating the constitution and contents of components.

Figure 16:
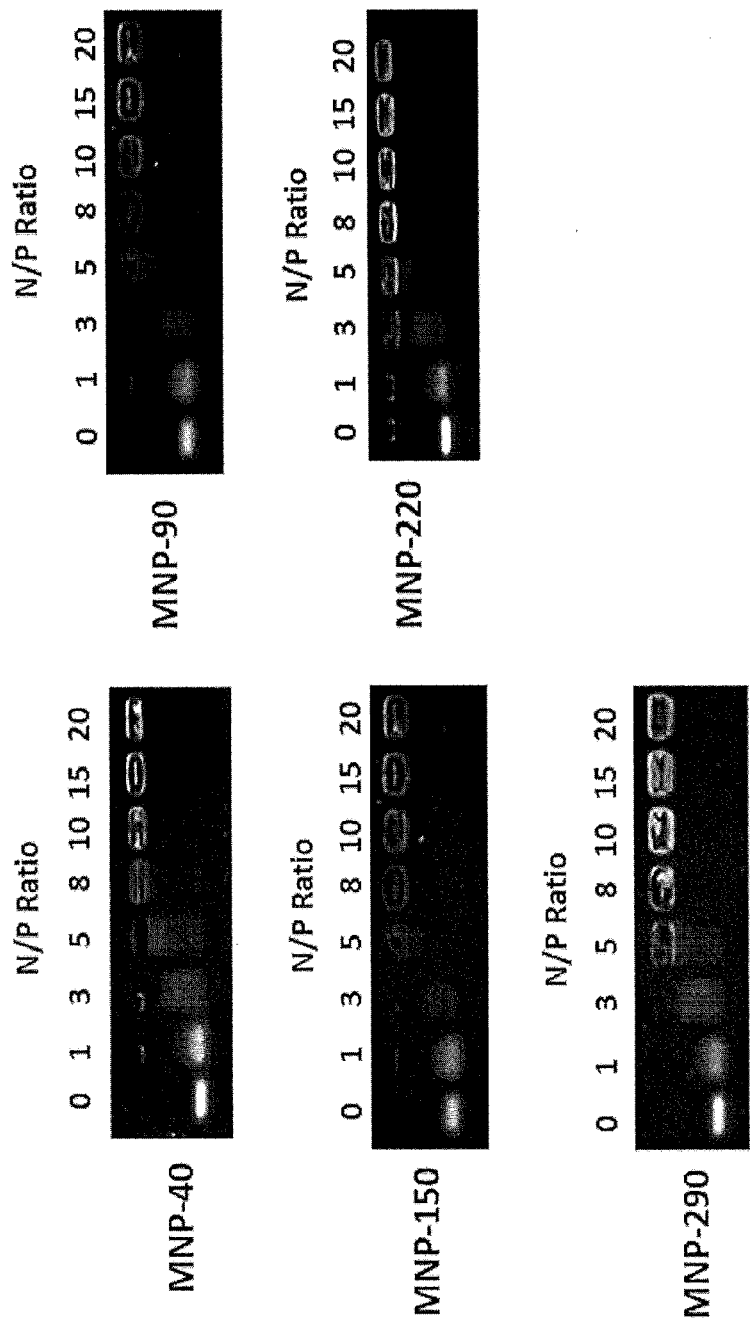
FIG. 16 shows the result of a gel retardation test for determining the siRNA-binding capacity of the mixed micellar particles consisting of three components: PCL$_{3300}$-PPEEA$_{3500}$, PCL$_{4400}$-PEG$_{2000}$ and PCL$_{3900}$.

(3) Determination of the Ability of the 3-Component Mixed Micellar Particles to Bind siRNA In order to determine the ability of the foregoing 3-component mixed micellar particles in binding siRNA, the binding between the 3-component micellar particles and siRNA was observed through gel-shift assay, in which the siRNA used was the siRNA in the negative control group in Example 3. The particular steps of the determination were as follows. Firstly, the foregoing 3-component mixed micellar particles of MNP-40, MNP-90, MNP-150, MNP-220 and MNP-290 were mixed with 20 pmol siRNA at N/P ratio of 0, 1, 3, 5, 8, 10, 15 and 20 respectively. After being mixed by sucking and blowing with a micropipettor, the mixture was kept standing at room temperature for 20 min. 1% agarose gel electrophoresis was used to detect the ability of the mixed nano-micelles in various sizes in binding siRNA. Electrophoresis was conducted in a TAE buffer solution (40 nM Tris-HCl, 1% acetic acid, 1 mM EDTA). Ethidium bromide (EB)-stained strips were photographed with a gel imager. The result is shown in FIG. 16. From FIG. 16, when N/P ratio was 5~8, all the foregoing 3-component mixed micellar particles of MNP-40, MNP-90, MNP-150, MNP-220 and MNP-290 fully binded with siRNA. This indicates the addition of PCL$_{3900}$ component doesn't generate obvious impact on the ability of the mixed micellar particles in binding siRNA.

What is claimed is:

1. A block copolymer, wherein the block copolymer is consisting of Block A and Block B, Block A is a polycaprolactone block, Block B is a polyphosphate block having the structural unit represented by Formula I,

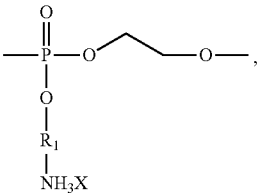

Formula I wherein, $R_1$ is an optionally substituted C2-C10 alkylene and X is a halogen;
in the block copolymer, the weight ratio between Block A and Block B is 1:0.1-5.3.

2. The block copolymer according to claim 1, wherein the polycaprolactone block has the structure represented by Formula II, and the block copolymer is an A-B diblock copolymer,

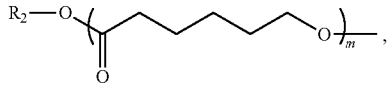

Formula II wherein, $R_2$ is an optionally substituted C1-C10 alkyl and m is an integer greater than 1; preferably, the average molecular weight of the polycaprolactone block is 500-40000.

3. The block copolymer according to claim 1, wherein the average molecular weight of the polyphosphate block is 500-10000.

4. A liquid composition, wherein the liquid composition contains water and micellar nano-particles, the micellar nano-particles are formed by a second block copolymer or by a first block copolymer and a second block copolymer together, wherein the first block copolymer is a polycaprolactone-polyethylene glycol block copolymer, the second block copolymer is the block copolymer according to claim 1, and the molar ratio between the first block copolymer and the second block copolymer is 0-100:1.

5. The liquid composition according to claim 4, wherein the particle diameter of the micellar nano-particles is 10-250 nm and the Zeta potential of the micellar nano-particles is 10-100 mV.

6. The liquid composition according to claim 4, wherein the first block copolymer is a polycaprolactone-polyethylene glycol diblock copolymer; wherein in the first block copolymer, the average molecular weight of the polycaprolactone block is 200-25000, and the average molecular weight of the polyethylene glycol block is 200-10000.

7. The liquid composition according to claim 6, wherein at least part of the polyethylene glycol block is modified by a targeting substance, and the targeting substance is at least one of a folic acid, a saccharide, an oligopeptide, a monoclonal antibody and an aptamer.

8. The liquid composition according to claim 7, wherein the saccharide is acetyl galactose.

9. The liquid composition according to claim 4, wherein, in the liquid composition, the concentration of the first block copolymer is $0-5\times10^{-3}$ M, and the concentration of the second block copolymer is $1\times10^{-5}-5\times10^{-3}$ M.

10. A method for preparing a liquid composition, wherein the method includes: contacting a second block copolymer with an organic solvent, or contacting a first block copolymer and a second block copolymer with an organic solvent, to obtain a first solution; and contacting the first solution with water under stirring, wherein the first block copolymer is a polycaprolactone-polyethylene glycol block copolymer, the second block copolymer is the block copolymer according to claim 1, the molar ratio between the first block copolymer and the second block copolymer is 0-100:1, and the organic solvent is miscible with water.

11. The method according to claim 10, wherein the organic solvent is at least one of dimethyl sulfoxide, acetonitrile and a C1-C6 alcohol.

12. The method according to claim 10, wherein the method further includes: dialyzing the solution obtained by contacting the first solution with water to remove the organic solvent therein.

13. A nucleic acid preparation, wherein the preparation comprises a nucleic acid as an active ingredient and a vector, wherein the vector is micellar nano-particles formed by a second block copolymer or by a first block copolymer and a second block copolymer together, the first block copolymer is a polycaprolactone-polyethylene glycol block copolymer, the second block copolymer is a block copolymer according to claim 1, the molar ratio between the first block copolymer and the second block copolymer is 0-100:1, and the molar ratio between the second block copolymer and the nucleic acid is 0.1-1000:1.

14. The nucleic acid preparation according to claim 13, wherein the molar ratio between nitrogen atoms in the vector and phosphorus atoms in the main chain of the nucleic acid is 1-100:1.

15. The nucleic acid preparation according to claim 13, wherein the particle diameter of the micellar nano-particles is 10-250 nm and the Zeta potential of the micellar nano-particles is 10-100 mV.

16. The nucleic acid preparation according to claim 13, wherein the first block copolymer is a polycaprolactone-polyethylene glycol diblock copolymer; wherein the average molecular weight of the polycaprolactone block is 200-25000 and the average molecular weight of the polyethylene glycol block is 200-10000.

17. The nucleic acid preparation according to claim 16, wherein at least part of the polyethylene glycol block is modified by a targeting substance, and the targeting substance is at least one of a folic acid, a saccharide, an oligopeptide, a monoclonal antibody and an aptamer.

18. The nucleic acid preparation according to claim 17, wherein the saccharide is acetyl galactose.

19. The nucleic acid preparation according to claim 13, wherein the nucleic acid is at least one of a siRNA, a microRNA, a shRNA, an antisense RNA and an aptamer.

20. A method of treating cancer in a human patient in need thereof, comprising administering a therapeutically effective amount of the nucleic acid preparation according to claim 13, to a cancerous tumor, in the human patient; wherein the cancer is selected from the group consisting of: lung cancer, prostate cancer, and liver cancer.

21. A method for preparing a block copolymer, wherein the method includes the following steps, (1) under conditions of ring-opening polymerization and in the presence of a ring-opening polymerization catalyst, contacting a polycaprolactone and the compound having the structural unit represented by Formula III with a first organic solvent, to obtain a first product,

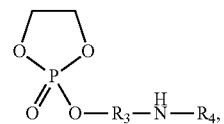

Formula III wherein, $R_3$ is an optionally substituted C2-C10 alkylene, $R_4$ is a protecting group of amino, and the weight ratio between the polycaprolactone and the compound having the structural unit represented by Formula III is 1:1-30;

(2) under an acidic condition, removing the protecting group of amino $R_4$ from the first product to obtain the block copolymer.

22. The method according to claim 21, wherein the polycaprolactone has the structural unit represented by Formula IV,

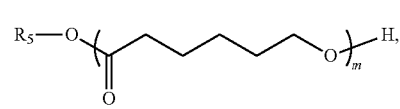

Formula IV wherein, $R_5$ is an optionally substituted C1-C10 alkyl and m is an integer greater than 1; preferably, the average molecular weight of the polycaprolactone is 500-40000.

23. The method according to claim 21, wherein the conditions of ring-opening polymerization include temperature of 20-50° C. and duration of 1-10 hours; the ring-opening polymerization catalyst is stannous iso-caprylate; and the first organic solvent is at least one of tetrahydrofuran, dimethyl sulfoxide and toluene.

24. The method according to claim 21, wherein the compound having the structural unit represented by Formula III is synthesized by: contacting the compound having the structural unit represented by Formula V with 2-chloro-2-oxo-1,3,2-dioxaphospholane under the condition of alcoholysis of acyl chloride,

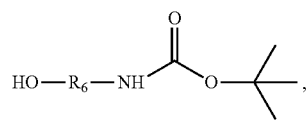

Formula V wherein, $R_6$ is an optionally substituted C2-C10 alkylene.

* * * * *